United States Patent [19]
Liu et al.

[11] Patent Number: 6,152,565
[45] Date of Patent: Nov. 28, 2000

[54] HANDHELD CORNEAL TOPOGRAPHY SYSTEM

[75] Inventors: David D. Liu, Irvine, Calif.; Joe Wakil; Ken Carbonari, both of Houston, Tex.; Greg Abbott, Spring, Tex.

[73] Assignee: Premier Laser Systems, Inc., Irvine, Calif.

[21] Appl. No.: 09/001,339

[22] Filed: Dec. 31, 1997

[51] Int. Cl.[7] ....................................................... A61B 3/10
[52] U.S. Cl. ............................................................. 351/212
[58] Field of Search .................................. 351/205, 208, 351/211, 212, 237, 247

[56] References Cited

U.S. PATENT DOCUMENTS

| | | | |
|---|---|---|---|
| 449,022 | 12/1891 | Reynolds | 351/211 |
| 4,692,003 | 9/1987 | Adachi . | |
| 4,705,037 | 11/1987 | Peyman et al. . | |
| 4,721,379 | 1/1988 | L'Esperanos . | |
| 4,863,260 | 9/1989 | Gerstein et al. . | |
| 5,212,505 | 5/1993 | Penney . | |
| 5,418,714 | 5/1995 | Server | 600/558 |
| 5,526,072 | 6/1996 | El Rage . | |
| 5,526,073 | 6/1996 | Mattioli | 351/212 |
| 5,528,323 | 6/1996 | Fujieda et al. . | |
| 5,585,873 | 12/1996 | Shalon et al. . | |
| 5,640,962 | 6/1997 | Jean et al. . | |
| 5,841,511 | 11/1998 | D'Souza | 351/212 |

FOREIGN PATENT DOCUMENTS

| | | |
|---|---|---|
| 0539068A1 | 4/1993 | European Pat. Off. . |
| 6-285024 | 10/1994 | Japan . |
| WO 89/01756 | 3/1989 | WIPO . |

*Primary Examiner*—George Manuel
*Attorney, Agent, or Firm*—Knobbe, Martens, Olson & Bear, LLP

[57] ABSTRACT

A corneal topography system incorporating a handheld unit, a base unit and a computer. The handheld unit includes a placido projector, a light source and a camera that receives the image of the placido image being reflected off of the patient's cornea. The light source is preferably comprised of a lightweight luminescent panel such as an EL panel. The handheld unit further includes a laser and a display that are used to properly align the handheld unit with respect to the patient's cornea into a desired orientation. The resulting reflected image is captured when the handheld unit is in the desired orientation and this image can then be used to obtain corneal topography data for the patient's eye.

41 Claims, 15 Drawing Sheets

HANDHELD TOPOGRAPHY FLOW CHART

HANDHELD CORNEAL TOPOGRAPHY SYSTEM

BACKGROUND OF THE INVENTION

1. Field of the Invention

The present invention relates to a system for measuring curvature of a patient's eye and, in particular, concerns a corneal topography system that includes a handheld unit for obtaining an image of a placido pattern reflected off of a patient's cornea.

2. Description of the Related Art

Over the past several decades, the increased use of surgical techniques and contact lens to correct vision problems has resulted in an increased need for data relating to the topography of the cornea of the eye. It is understood that, deformations in the cornea of a patient's eye are largely responsible for vision problems experienced by a particular patient. Specifically, the shape of a patient's cornea is a significant contributing factor to such common eye diseases such as myopia. Generally, an eye with perfect vision has a near spherical cornea so that incident light is defracted inward towards a focal point in within the eye. Variations in the shape of the cornea can result in light not being defracted into the focal point of the eye thereby producing visions problems for the patient. These eye problems are typically corrected by positioning a lens, either a spectacle lens or a contact lens, in front of the eye that is configured to be able to correct for the deformations in the patient's cornea which are causing the eye problem.

In the past, ophthalmologists determined the correction needed by a particular patient empirically by positioning a series of lenses in front of the patient's eye until their vision improved. However, as analytic techniques and instruments have become more sophisticated, mapping of the cornea to obtain the overall contour of the cornea, has become more common. Corneal topography data provides a treating physician with information as to the localized radius of curvature of a particular cornea. This allows the treating physician to more accurately select contact lenses and it also greatly aids a treating physician in correcting eye deformations through surgical techniques.

In the past decade, the use of surgical techniques to correct eye problems such as myopia, have become significantly more common. Techniques such as radial keratotomy and other well-known techniques, require that the treating physician have detailed information as to the configuration of the patient's cornea. With this information, the treating physician can then cut, ablate, or otherwise change the outer surface of the cornea at various locations to alter the overall shape of the cornea to thereby correct the patient's vision. In fact, these techniques have become significantly advanced so that treating physicians are able to correct significant nearsightedness or far-sightedness to near perfect vision.

It is, of course, understood that the treating physician will need detailed corneal topography information to perform these surgical techniques and also to fit contact lenses in specific situations. As a consequence, corneal topography systems have been developed which provide detailed information about the topography of the outer surface of a patient's cornea. One such system is disclosed in U.S. Pat. No. 5,863,260 to Gersten et al. The system disclosed in U.S. Pat. No. 4,863,260 is typical of most currently available corneal topography systems. Specifically, corneal topography systems generally project into the patient's eye, a placido image which is an image of a plurality of concentric rings or mires. The image of these mires is reflected off of the patient's cornea and is then captured using a camera. Hence, the camera obtains a two-dimensional image of the mires being reflected off of the patient's three dimensional cornea. The position of the reflected mires in the captured image can then be used to calculate the curvature of the patient's eye.

Specifically, it is assumed that a cornea having perfect vision will be generally uniformly spherical. If the placido image was reflected off of a perfectly spherical surface, the reflected mires would appear on a two-dimensional image as a plurality of concentric rings with the two dimensional locations of the rings being related to the curvature of the spherical surface. If, however, the patient's cornea is not perfectly spherical, the positions of the plurality of mires in the resulting reflected image are generally displaced from the corresponding position of the mires that is reflected off of the perfect sphere. A comparison of the position between the image reflected off of the patient's cornea and a corresponding perfect sphere, will permit the determination of the deviation of the patient's cornea from a perfect sphere. In this manner, the radius of curvature of the patient's cornea at locations over the entire surface area of the patient's eye can be calculated thereby providing the topography of the patient's cornea.

It is understood that to accurately calculate the corneal topography data of a patient's eye, it is desirable that the patient's eye be positioned in a specific orientation with respect to the placido projector and the camera that is obtaining the image. This specific placement is required as the corneal topography data is obtained by comparing the image of the patient's cornea to an image that is reflected off of a corresponding calibration sphere. For the comparative analysis to be accurate, it is desirable that the patient's cornea be located in the same or corresponding orientation as the calibration sphere was when the calibration data was obtained. Consequently, most corneal topography systems include mechanisms for ensuring that the cornea is in the correct orientation with respect to the placido projector and the camera. In most systems, the placido projector is positioned so that the axis of the placido projector intersects the apex of the patient's cornea, i.e., is coincident with the optical axis of the patient's cornea. Similarly, the camera that receives the reflected image is also located so as to receive the image along the optical axis which intersects the apex of the patient's cornea. Moreover, the placido projector and the camera are also positioned along the optical axis so that the apex of the patient's eye is positioned a known distance from the camera. This known distance corresponds to the distance that the camera was positioned from the apex of the perfect sphere when the corresponding calibration data was obtained.

It will be appreciated that the requirements of specifically positioning the patient's cornea with respect to the corneal topography machine has resulted in the corneal topography machine being a very large and complex instrument. Specifically, complicated mechanisms are usually attached to the placido projector and camera so that an operator can accurately locate the placido projector and camera in the correct orientation with respect to the apex of the patient's cornea.

A further difficulty with prior art corneal topography systems is that the placido projector generally has to incorporate numerous lamps so that the placido projector is uniformly illuminated over its entire surface area. In some devices, the placido projector is comprised of a generally conical or parabolic projector that is six or eight inches in diameter at its outer end. Inside of the cavity defined by the projector, a plurality of concentric opaque rings and mires are formed on a translucent background. The light sources must be located so as to uniformly illuminate the translucent material so that the placido image can be projected onto the patient's eye. It will be appreciated that the light system used to illuminate such a placido projector requires a significant amount of space and also adds to the complexity of the corneal topography system.

For these reasons, corneal topography systems are generally expensive and complex systems that occupy a significant amount of space in an ophthalmologist's office. The room occupied by the corneal topography system and the expense of the systems generally limits the number of systems that are purchased by an ophthalmologist. Consequently, patient treatment is often bottlenecked by the existence of a limited number of corneal topography systems.

Moreover, it would be desirable to be able to asses corneal topography during or immediately following eye surgeries. As discussed above, nearsightedness and farsightedness are often corrected by changing the shape of the cornea. This typically requires that the patient be prone on an operating table during the surgery. In this position, it is generally not possible to obtain any corneal topography data. Further, the patient is generally not in a condition where they can be taken to another location to obtain the corneal topography data during the actual surgery. Hence, while existing corneal topography systems have some utility for surgeons engaged in vision correction procedures, the utility is limited by the lack of portability of the systems.

From the foregoing, it can be appreciated that there is a need for a corneal topography system which is smaller and more portable. To this end, there is a need for a corneal topography system that has a handheld component which can be carried by an operator while still allowing the operator to precisely located the handheld unit in the desired orientation with respect to the patient's eye. To this end, the handheld unit should include a placido projector with a light source that is sufficiently lightweight and compact so as to allow. The operator to correctly position the placido projector in the desired orientation with respect to the patient's eye and maintain the projector in this orientation while capturing the reflected image. The light source should, of course, still uniformly illuminate the placido projector so as to produce a high quality image on the patient's eye.

SUMMARY OF THE INVENTION

The aforementioned needs are satisfied by the corneal topography system of the present invention which is comprised of a handheld unit having a placido projector and a camera and a base unit which receives an image that is obtained by the camera of the handheld unit. The handheld unit incorporates the placido projector which is illuminated by a light source which, in one embodiment, is comprised of a luminescent light tape that is positioned adjacent the placido projector. The handheld unit can be positioned in front of the patient's eye in the desired orientation and, in one embodiment, the handheld unit automatically initiates the capture of an image of the placido mires reflecting off of the patient's eyes when the handheld unit is in a desired orientation with respect to the patient's eye. The image can then be provided to the base unit where the image can be further processed to produce corneal topography data.

In one embodiment, the system includes a base unit and a personal computer which receives information from the handheld unit via the base unit. The base unit incorporates a frame grabber adapted to capture the placido image reflected off the patient's cornea in response to the handheld unit being correctly oriented with respect to the patient's cornea. The personal computer in this embodiment receives the captured image and does verification processing to ensure that the captured image was taken with the handheld unit being in a desired orientation with respect to the patient's cornea. Following image verification the personal computer can then perform further processing to determine radius of curvature and other corneal topography data from the captured image.

In one embodiment of the invention, the handheld unit includes an LCD display which receives an image from the camera of the placido image being reflected from the patient's cornea. The operator can then correctly orient the handheld unit with respect to the patient's eye by viewing the image of the reflected image and patient's cornea in the LCD.

In one embodiment, the placido projector is made of a translucent material and has a generally conical shape and defines an inner cavity. A plurality of opaque mires are preferably positioned within the inner cavity. At the center of the placido projector, an opening is formed which is positioned to allow the reflected image to pass through the central axis of the placido projector so as to be received by the camera. The LCD display includes a targeting mechanism, such as a pair of inscribed cross-hairs, that is formed so that when an alignment axis of the handheld unit is aligned with optical axis of the patient's eye, the cross-hairs are generally centered in the center of the innermost mire of the reflected image that is being displayed to the user on the LCD. In this fashion, the operator can correctly orient the handheld unit in the x and y planes with respect to the apex of the patient's cornea.

In another aspect of this embodiment of the invention, the targeting mechanism includes a light source, such as a laser, which reflects off of the patient's cornea and a light detector which receives the reflected light. When the handheld unit is in the correct orientation along an axis normal to the apex of the cornea, the light source reflects the light off of the apex of the patient's cornea and the light sensor provides an indication that the handheld unit is in the correct orientation along this axis. In one embodiment, the system is adapted to automatically capture the reflected image when the sensor indicates that the handheld unit is located a desired distance along the normal axis from the apex of the patient's cornea.

A corneal topography system comprising a handheld unit incorporating a camera, a placido projector and a light source positioned within a casing that is sized so as to be movable by an operator by hand wherein the placido projector projects a placido image when the light source is illuminated and wherein the video camera obtains an image of the placido image reflecting off of a patient's cornea when the handheld unit is positioned adjacent the patient's cornea, an orientation alignment mechanism that is coupled to the handheld unit, wherein the orientation alignment mechanism facilitates alignment of the handheld unit with respect to the patient's cornea so that when the handheld unit is in a first relative orientation with respect to the patient's cornea, the orientation alignment mechanism provides a first signal indicative thereof, and an image capture system that receives (1) signals from the camera indicative of the placido image reflected from the patient's cornea and (2) the first signal from the orientation alignment mechanism wherein the image capture system, upon receiving the first signal from the orientation alignment mechanism, captures the camera signals that correspond to the moment that the handheld unit was in the first orientation with respect to the patient's cornea wherein the captured reflected placido image is indicative of the corneal topography of the patient's cornea; a corneal topography system comprising a handheld housing defining a first and a second axis that are orthogonal to each other and further defining a mounting cavity wherein the first axis extends through the mounting cavity, a placido projector positioned within the mounting cavity of the handheld housing, wherein the placido projector is at least partially formed of a translucent material so as to be able to project a placido image when illuminated from a first surface and wherein the placido projector has a camera opening positioned at substantially the center of the placido projector, a light source comprised of a flexible electro-luminescent panel that is positioned within the mounting cavity in the handheld unit so as to be interposed between the first surface of the placido projector and the mounting cavity and so as substantially cover the first surface of the placido projector, wherein the light source illuminates the placido projector to induce the placido projector to project the placido image, a camera mounted within the housing so as to receive through the camera opening in the placido projector a reflected placido image reflected off of a patient's cornea that occurs when the placido projector is illuminated and the handheld housing is positioned adjacent the patient's cornea wherein the camera provides camera signals indicative of the reflected placido image, a display mounted on the handheld unit, that receives the camera signals and displays to the operator the reflected placido image, the display incorporating at least one alignment indicator that is positioned on the display so that the operator can move the handheld unit to orient the indicator with respect to the displayed reflected placido image into a first orientation, wherein the indicator is positioned with respect to the housing so that when the indicator is in the first orientation, the first axis of the handheld unit is in a pre-determined relationship with an optical axis of the patient's cornea and an image capture system that receives the camera signals wherein the image capture system captures the camera signals of the reflected placido image when the first axis of the handheld unit is in the predetermined relationship with the optical axis of the patient's cornea wherein the captured reflected placido image is indicative of the cornea topography of the patient's cornea, and a method of obtaining corneal topography data comprising positioning a placido projector mounted in a handheld unit adjacent a patient's cornea, illuminating the placido projector by inducing an electro-luminescent panel positioned adjacent the placido projector to luminesce, sensing with a camera a reflected placido image reflected off of the patient's cornea, displaying the reflected placido image on a display attached to the handheld unit, moving the handheld unit until an indicator formed on the display is positioned on the displayed image in a pre-selected relationship that results in the camera being in a first orientation with respect to an axis extending through the apex of the patient's cornea, moving the handheld unit along the axis extending through the apex of the cornea, while keeping the indicator in the pre-selected relationship with the displayed image until the handheld unit is in a pre-selected relationship along the axis with respect to the patient's cornea, automatically capturing the reflected placido image when the indicator is in the preselected relationship with the displayed image and when the handheld unit is in the pre-selected relationship along the axis to the patient's cornea; and comparing the positions of a plurality of points on the reflected placido image to data representative of corresponding points on calibration models to determine the corneal topography of the cornea at the plurality of points.

It will be appreciated that the embodiments of the present invention allows for a doctor to use a handheld instrument containing a placido projector having a plurality of concentric mires and a camera to obtain an image of the patient's eye having a plurality of reflected mires superimposed thereon. The unit is lightweight and compact as it contains a lightweight and compact placido projector with a lightweight and compact light source. Moreover, the system automatically triggers the capturing of the image when the system ascertains that it is in the desired orientation with respect to the apex of the patient's eye. Consequently, the system of this embodiment of the present invention is capable of obtaining corneal topography data using a handheld device which enhances the flexibility of use of the corneal topography system in the ophthalmologist's office. These and other objects and advantages of the present invention will become more fully apparent from the following description taken in conjunction with the accompanying drawings.

DETAILED DESCRIPTION OF THE PREFERRED EMBODIMENT

Figure 1:
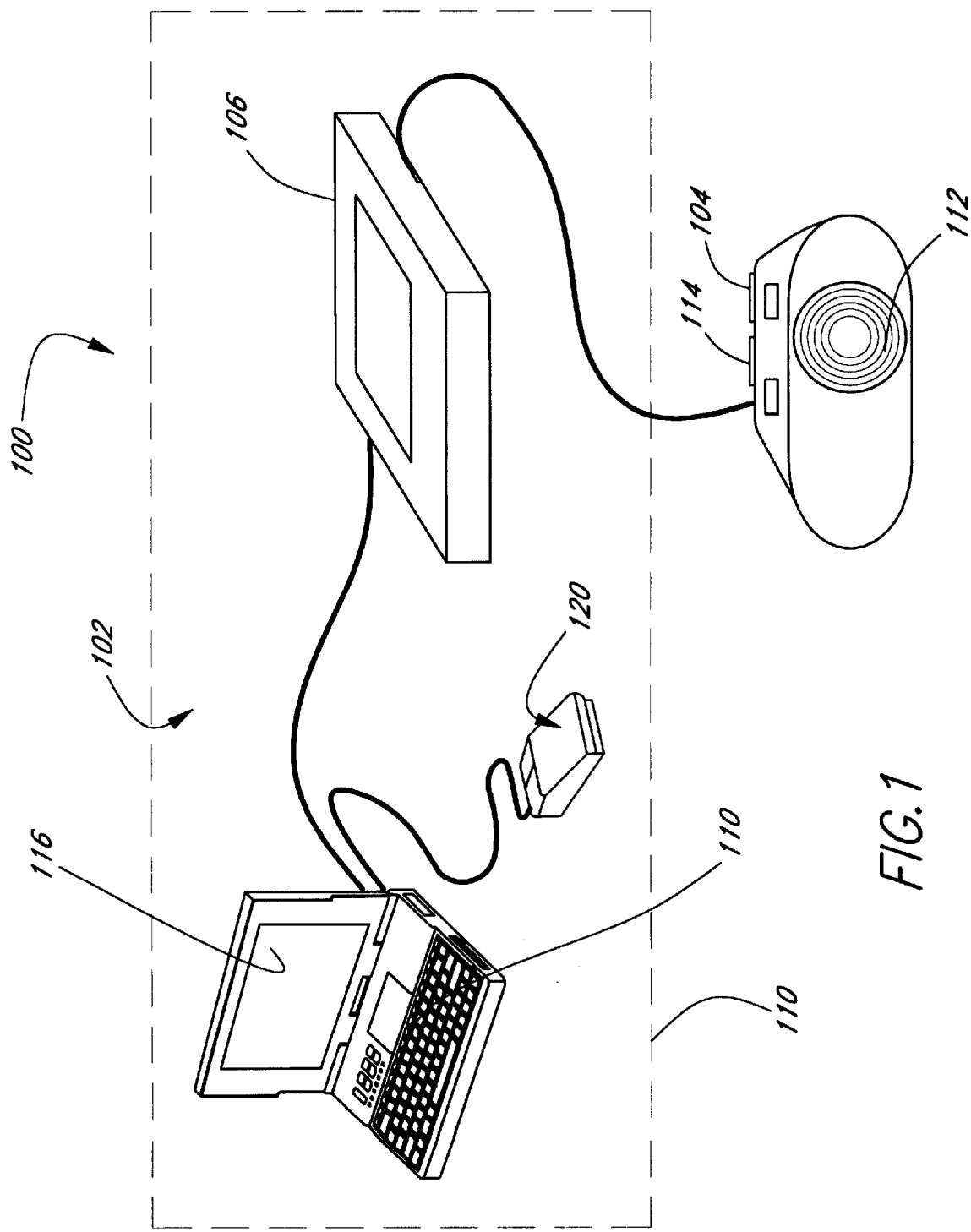
FIG. 1 is a perspective view illustrating the basic components of one embodiment of the corneal topography system of the present invention.

Reference will now be made to the drawings wherein like numerals refer to like parts throughout. FIG. 1 illustrates the basic components of one embodiment of the corneal topography system 100 of the present invention. The corneal topography system 100 includes a computer 102, such as an IBM PC or an equivalent, or even a portable computer as shown, a handheld unit 104 and a base unit 106 that is adapted to receive the handheld unit 104 and also provides an interface between the personal computer 102 and the handheld unit 104. Collectively, the personal computer 102 and the base unit 106 may comprise a main base unit 110 that receives images of mires reflecting off of the patient's cornea obtained by the handheld unit and analyzes these images and develops the corneal topography data that can be used by a treating physician.

Figure 11:
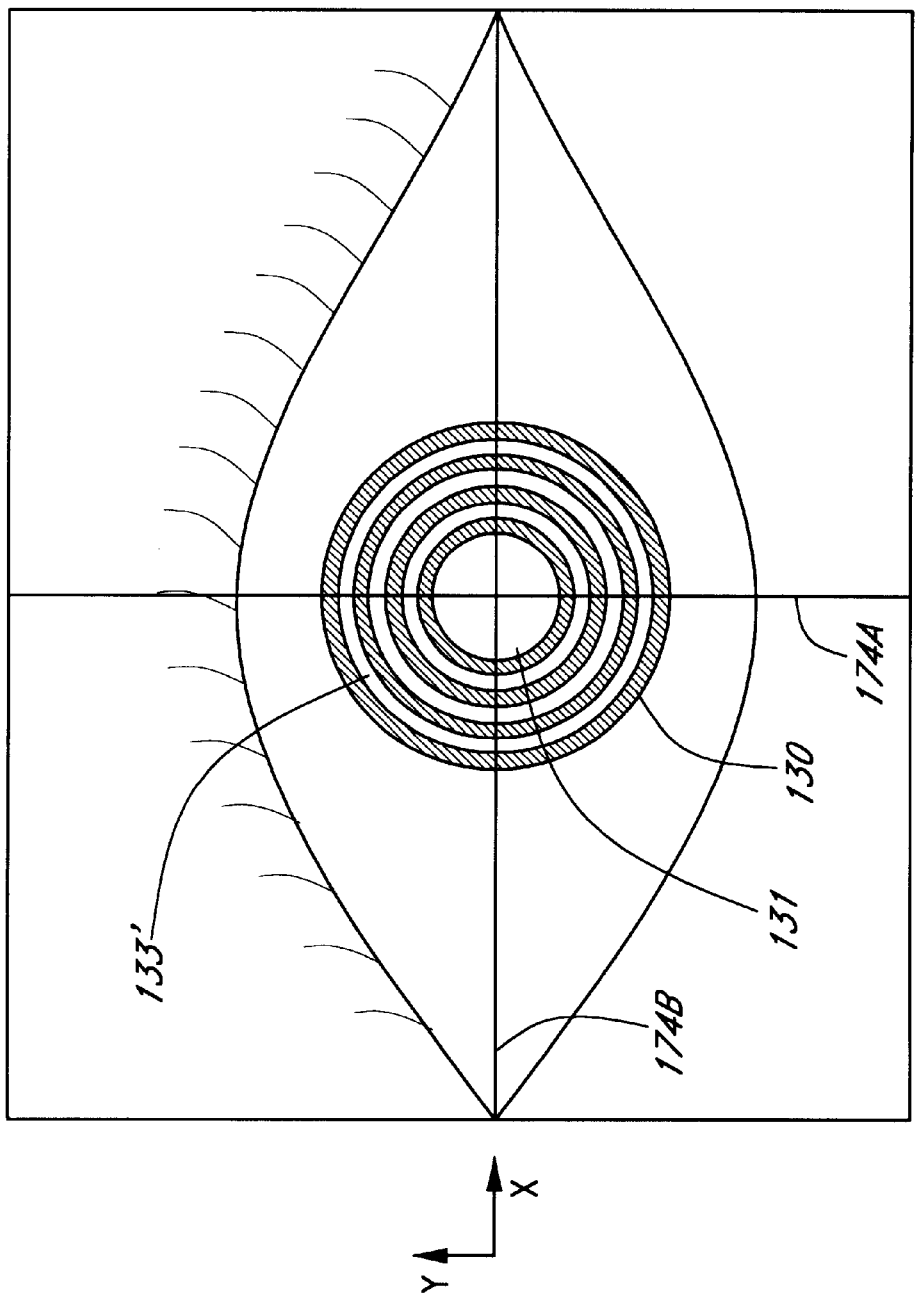
FIG. 11 is a schematic illustration illustrating a reflected placido image reflected off a patient's eye as seen by the operator when looking at the image via an LCD display incorporated in the handheld unit of corneal topography system of FIG. 1.

The handheld unit 104 is sized and dimensioned so as to allow an operator to position the handheld unit 104 in a desired relation with respect to a patient's eye. The handheld unit 104 includes a placido projector 112 which will project a placido image comprised of a plurality of mires onto a patient's eye (See, e.g., FIG. 11) in a well-known manner. As will be discussed in greater detail below, the handheld unit 104 incorporates a camera which receives the placido image reflected off of the patient's cornea and provides this image to an LCD display 114 to allow the operator to correctly orient the handheld unit 104 with respect to the patient's cornea. When the handheld unit 104 is correctly oriented, the corneal topography system 100 captures the reflected image and provides the reflected image to the computer 102 via the base unit 106 to allow the computer to perform cornea topography analysis in a well known manner. In this embodiment, the handheld unit 104 is connected to the base unit 106 via a long flexible cord using a fixed wire serial interface which could include an RS-232 type interface. Hence, the operator can pick up and carry the handheld unit 104 to the patient's location. This eliminates the need for a portion of the ophthalmologist's office to be reserved for only a corneal topography station and further allows the corneal topography system to be used to obtain corneal topography data during surgical procedures with the patient being positioned in the operating room. It will be appreciated from the following description that the handheld unit 104 can be used to obtain corneal topography data while the patient is positioned in an ordinary ophthalmologist's chair or even prone on an operating table.

The base unit 106 is then connected to the personal computer 102 via a dual parallel port connection in a well-known manner. Hence, the personal computer 102 does not even have to be located in the same room as the handheld unit 104. Moreover, the handheld unit 104 also does not have to be located in the same room as the base unit 106 which further enhances the flexibility of using the corneal atopography system 100. The personal computer 102 incorporates a display 116 and input devices such as a keyboard 110 or mouse 120. In this embodiment, the personal computer 102 is preferably any of a number of currently available portable computers. In fact, the use of a portable computer may be preferred as it further increases the flexibility of use of the computer 102 in that the entire system can then be portable between rooms. It will be understood from the following discussion that the handheld unit 104 and the base unit 106 are very small in size, e.g., approximately telephone size and collectively weigh only several pounds. Consequently, the system 100 as a hole can easily be transported from room to room, particularly if the computer 102 is selected to be a portable type computer.

Figure 2:
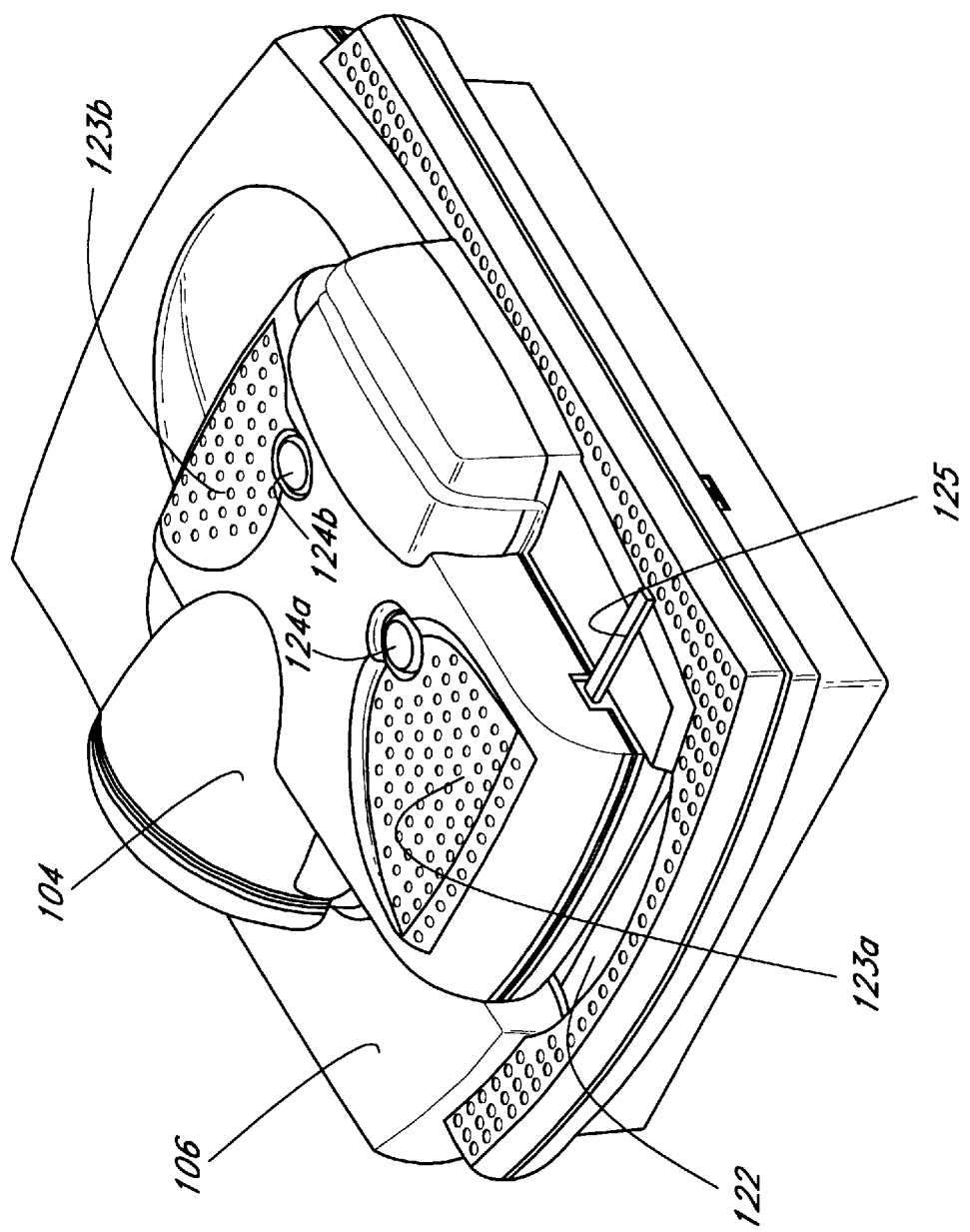
FIG. 2 is a perspective view illustrating a handheld unit nestled in an accompanying base unit of the handheld corneal topography system of FIG. 1.

FIG. 2 is a perspective view of the handheld unit 104 positioned within a receptacle 122 formed in the base member 106. As shown, the receptacle 122 is sized so as to allow the handheld unit 104 to be stored within the receptacle 122 of the base unit 106 in a secure fashion. As is also illustrated in FIG. 2, the handheld unit 104 includes a cord-type connector 125 including an RS-232 interface which interconnects the handheld unit 104 to the base unit 106. Moreover, the handheld unit 104 includes a left and right operator switch 124a and 124b which the operator depresses when initiating an image capture sequence in the manner that will be described below. The handheld unit 104 is preferably held by the operator with two hands so that the operator is looking into the LCD display 114 with their hands positioned on the hand locations 123a and 123b and with their fingers positioned adjacent the buttons 124a and 124b. In the preferred embodiment, the handheld unit 104 is approximately 5¾ inches wide, 7¾ inches long and 3½ inches thick and weighs less than two pounds. By holding the handheld unit 104 in two hands, the operator is able to position the placido projector 112 in a desired orientation with respect to the patient's cornea in order to obtain a placido image reflected from the patient's cornea that can be further analyzed by the system 100 to provide corneal topography data in the manner discussed in greater detail below.

As shown in FIG. 2, the handheld unit 104 is shaped in a manner similar to a pair of binoculars. As will be discussed below, the optics in the handheld unit 104 are configured so as to extend in a direction normal to the direction of the axis of the patient's cornea. This makes the unit more compact as it generally extends horizontally. The overall length of the unit is therefore shorter which means that the operator can obtain images of the patient's cornea with the patient in a number of positions such as being positioned in an examination chair or even lying prone on an operating table. The operator simply has to position the handheld unit 104 on the axis of the eye in the manner that will be described in greater detail below. Consequently, the operator can more easily maneuver the handheld unit 104 which aids in the use of the corneal topography system 100 in compact environments such as operating rooms and the like.

Figure 3A:
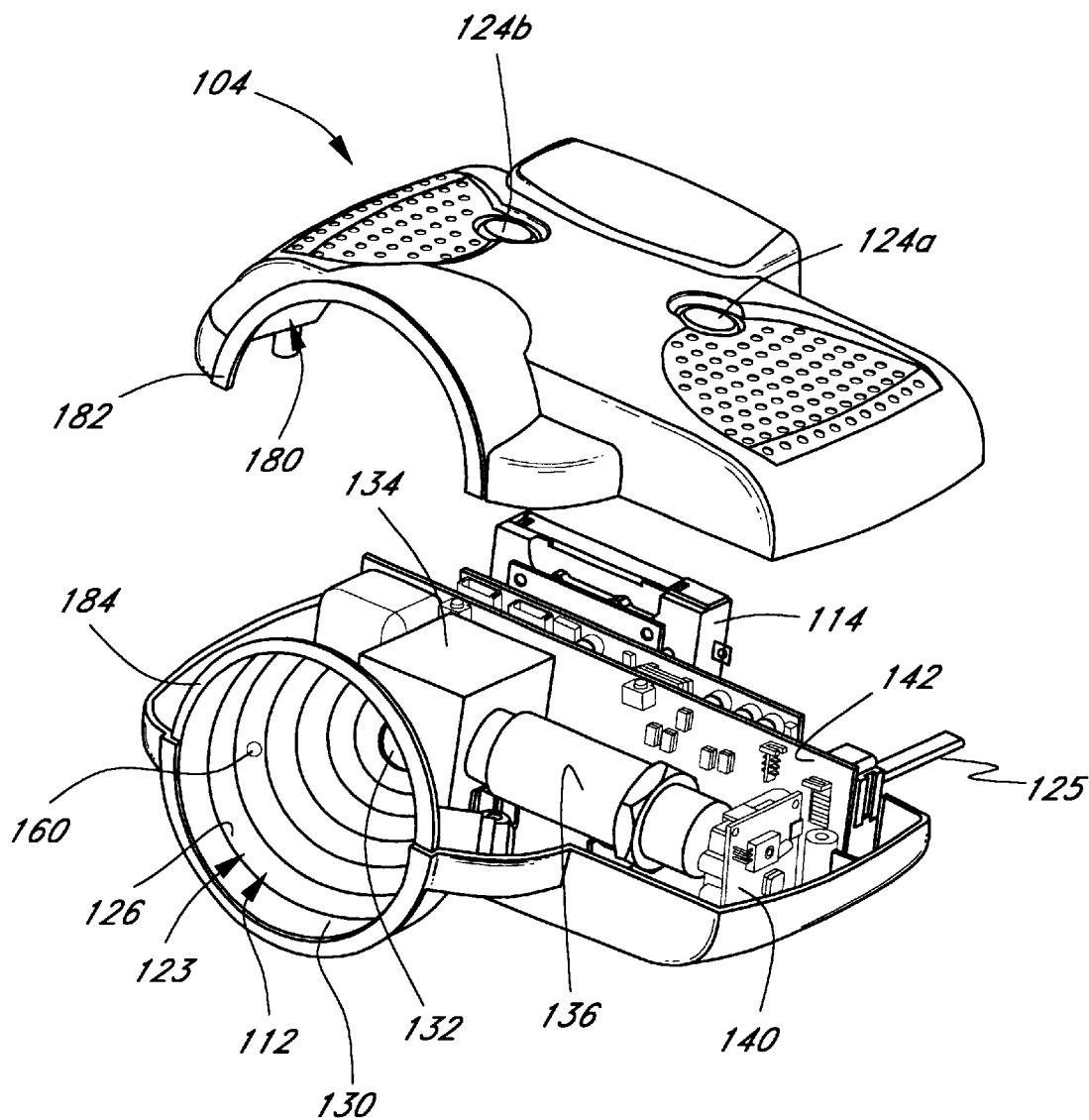
FIG. 3A is a front perspective view of the handheld unit of the corneal topography system of FIG. 1 with the cover partially removed so as to illustrate the components positioned therein.

FIG. 3A illustrates the front of the handheld unit 104 in greater detail. As shown in FIG. 3A, the handheld unit 104 defines a cavity 123 that contains the placido projector 112. The placido projector 112 is comprised of a cone of translucent material wherein the inner surface of the placido projector 112 is coated with a plurality of concentric opaque mires 130. As will be discussed in greater detail below, a light source illuminates the translucent material comprising the placido projector 112 so that an image of a plurality of concentric opaque mires is projected out of the cavity 123. The inner end of the placido projector 112 includes an opening 132 that, when handheld unit 104 is positioned in front of the patient's cornea, receives a reflected image which comprises the patient's cornea and the image of the plurality of the mires reflected off of the patient's cornea so as to be superimposed on the image of the patient's cornea. The opening 132 provides the reflected image to a prism 134 which then in turns reflects this image through optics 136 to a CCD camera 140. The CCD camera 140 then provides an analog signal to the LCD display 114 and also provides the data to the base member 106 via the serial interface 125 in a well-known manner. The handheld unit 142 also includes various power supplies that are mounted on PC boards 142 positioned within the handheld unit 104.

Figure 3B:
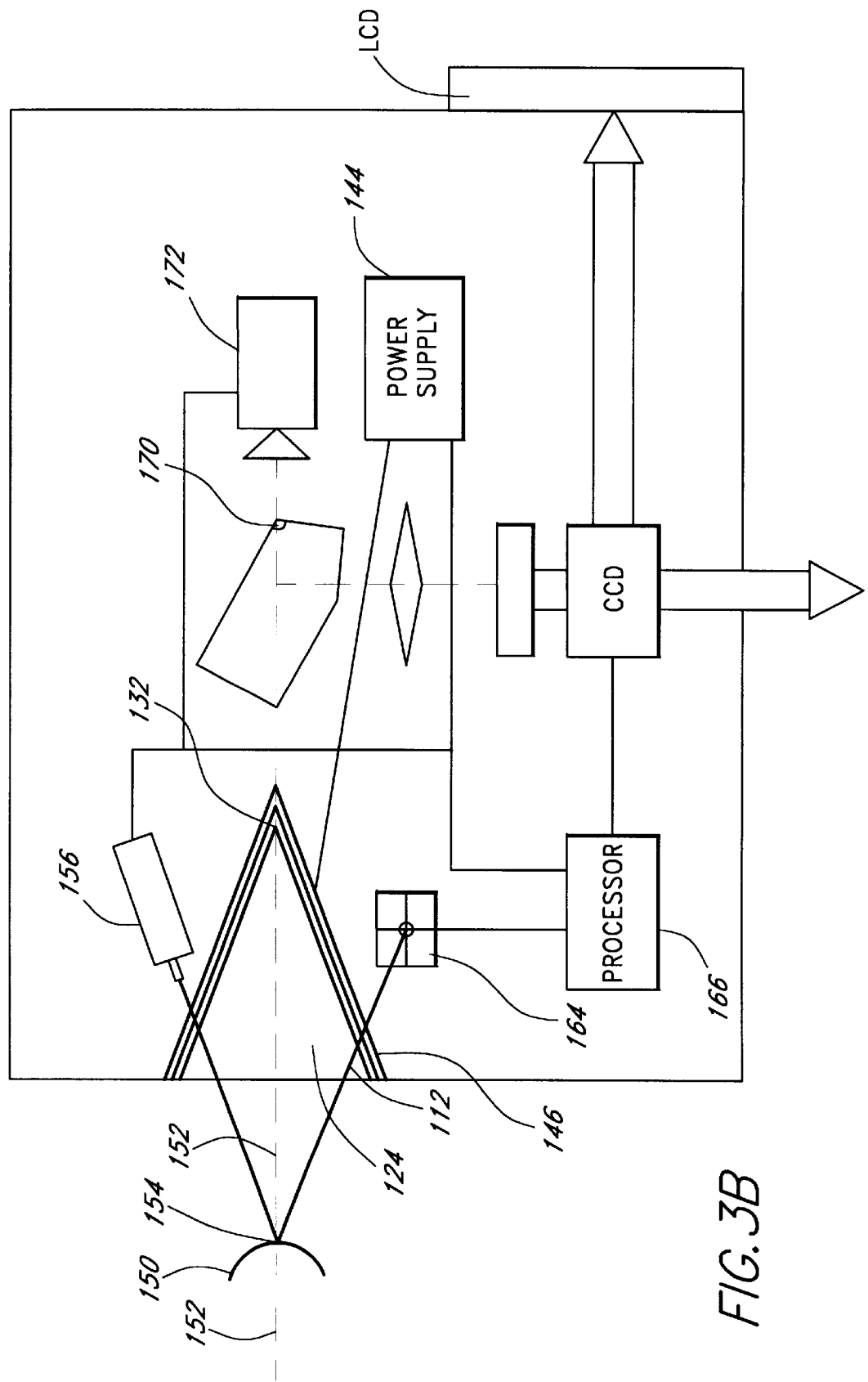
FIG. 3B is a schematic illustration illustrating some of the various components of the handheld unit of FIG. 3A.

Specifically referring to FIG. 3B, the handheld unit 104 incorporates one or more power supplies 144 that power a light source 146 that illuminates the translucent material of the placido projector 112. In this embodiment, the light source 146 is comprised of an Electro-luminescent panel, known as an EL panel 190 such as a Nova Light Printed EL Panel with white phosphor such as those available from Electroluminescent Technology Corporation of Austin, Tex. The EL panel 190 is wrapped around an outer surface of the placido projector 112 so that when powered, the translucent areas of the placido projector 112 are illuminated.

The handheld unit 104 is preferably positioned by the operator so that the placido projector 112 is positioned in a known orientation with respect to the cornea 150 of a patient's eye. Specifically, the placido projector 112 is preferably positioned so that the optical axis 152 of the patient's eye coincides with the axis 135 (FIG. 5B) of the inner cavity 124 of the placido projector 112. In this embodiment, the optical axis 152 comprises an axis extending perpendicularly out of a plane tangent to the apex 154 of the patient's cornea 150. Moreover, the opening 132 in the placido projector is also preferably located a known distance along the optical axis 152 from the apex 154 of the patient's cornea. It will be appreciated from the following discussion that, while alignment of the axes 152 and 135 is the preferred manner of correctly orienting the handheld unit 104 with respect to the cornea 150, that any of a number of different relative orientations of the handheld unit 104 to the cornea 150 can be used so long as the relative orientation between the two objects is known to thereby permit mathematical adjustments in the resulting calculations.

To facilitate the alignment of the placido projector 112 along the optical axis 152, a laser 156 shines a light through an opening 160 (see FIG. 3A) so as to be reflected off of the cornea 150 of the patient's eye. The reflected light is then incident upon a detector 164, which in this embodiment is a quadrature detector, and the laser 156 and quadrature detector 162 are positioned and oriented so that when the laser light 156 is incident on the apex of the patient's eye, the quadrature detector 160 provides a signal to a processor 260 (FIG. 7) indicating that the handheld unit 104 is located in the desired orientation along the optical axis 152 from the apex 154 of the patient's cornea 150. It will, of course, be appreciated that any of a number of light sources and detectors can be used in the place of the laser and quadrature detector without departing from the spirit of the present invention. This alignment process will be described in greater detail below in reference to FIGS. 9 and 10.

In this embodiment, the laser is a Visible Laser Diode of a type commonly available that operates at approximately 180 microwatts for a maximum of 20 seconds so as to not damage the patient's eye. The quadrature detector 164 is a quadrature detector which is approximately 2 square mm such as the quadrature detectors available from Photonic Detectors, Inc. of Simi Valley, Calif. As will be discussed in greater detail below, when the quadrature detector 164 indicates that the placido projector 112 is located at the desired distance along the optical axis 152, the handheld unit 104 then initiates capture of the image of the patient's cornea and the reflected mires 130 as they are reflected off of the patient's cornea 150 along the optical axis 152 through the opening 132.

Specifically, the reflected image is reflected through the opening 132 into the prism 134 which, in this embodiment, is preferably comprised of a pentaprism that reflects the light twice so as to invert the reflected image and also so as to reflect the light into the optics 136 in a direction that is at a right angle to the optical axis 152. Reflecting the light in this manner using the pentaprism results in the reflected image received by the camera 140 being a non-inverted image and also permits the handheld unit 104 to be more compact as the camera 140 can be mounted at a right angle to the optical axis 152. Reflecting the light twice in this manner results in the overall light results in the handheld unit 104 being more compact. Specifically, the light is reflected twice in the compact pentaprism 134. This reflection reduces the overall length of the path that the reflected image must travel to the camera 140 by the length of the path of reflection within the prism. In this embodiment, the prism 134 used results in the light being reflected along approximately a one inch path within the prism.

Hence, the overall dimensions of the handheld unit 104 can be reduced by a corresponding amount to reduce the overall size of the unit thereby enhancing the portability and flexibility of use of the unit 104. Moreover, as the pentaprism 134 reflects the light of the reflected image at an angle that is normal to the optical axis, the overall length of the unit 104 can be reduced as the optics 136 and the camera 140 are positioned horizontally with respect to the optical axis. A decrease in the overall length of the device further increases the flexibility of use of the handheld unit 104 as the operator can more easily correctly orient the device in confining environments such as during eye operations.

In this embodiment, the pentaprism 134 is a five-sided prism that reflects light rays through a 90° angle by two reflections. The reflecting surfaces are aluminized although an opening 170 is formed in one surface of the pentaprism so as to allow a fixation light 172 to be beamed through the prism 170 so as to emanate out of the opening 132 in the placido projector 112. The fixation light 172 provides a light for the patients to focus on when the operator is positioning the handheld unit 104. The pentaprism in this embodiment is available from the Edmond Scientific Company of Berington, N.J.

The reflected image of the mires is then passed through the focussing optics 136 to the CCD camera 140. In this embodiment, the CCD camera is a ⅓-inch CCD board camera that has 380 TV lines of horizontal resolution by 350 vertical TV lines of resolution. The specific camera used in this embodiment is a Type EM 200 camera available from Computar of New York. Moreover, the focussing optics 136 are preferably selected so as to optimize the clarity of the reflected image received by the cornea 140.

As will be discussed in greater detail below, when the handheld unit 104 is turned on, the light source 146 is powered up which results in the placido projector 112 projecting the placido image onto the patient's cornea. The reflected placido image is provided to the CCD camera 140 which then in turn provides the image to the LCD display 114. Hence, the operator views the patient's cornea and the reflected placido image in the LCD 114 display and uses this reflected image to correctly orient the handheld unit 104 with respect to the apex 154 of the patient's cornea 150 in a manner that will be described in greater detail below. The laser 156 is continuously beaming a laser beam onto the patient's cornea so that the quadrature detector 164 can receive the reflected laser beam. When the quadrature detector 164 indicates that the handheld unit 104 is in the desired orientation along the optical axis 152 from the apex 154 of the cornea 150, the corneal topography system 100 then institutes a process whereby the reflected image of the placido image and the patient's cornea 150 is captured. The captured image can then be compared to calibration data so that the corneal topography data can be developed in a well-known manner.

Figure 3C:
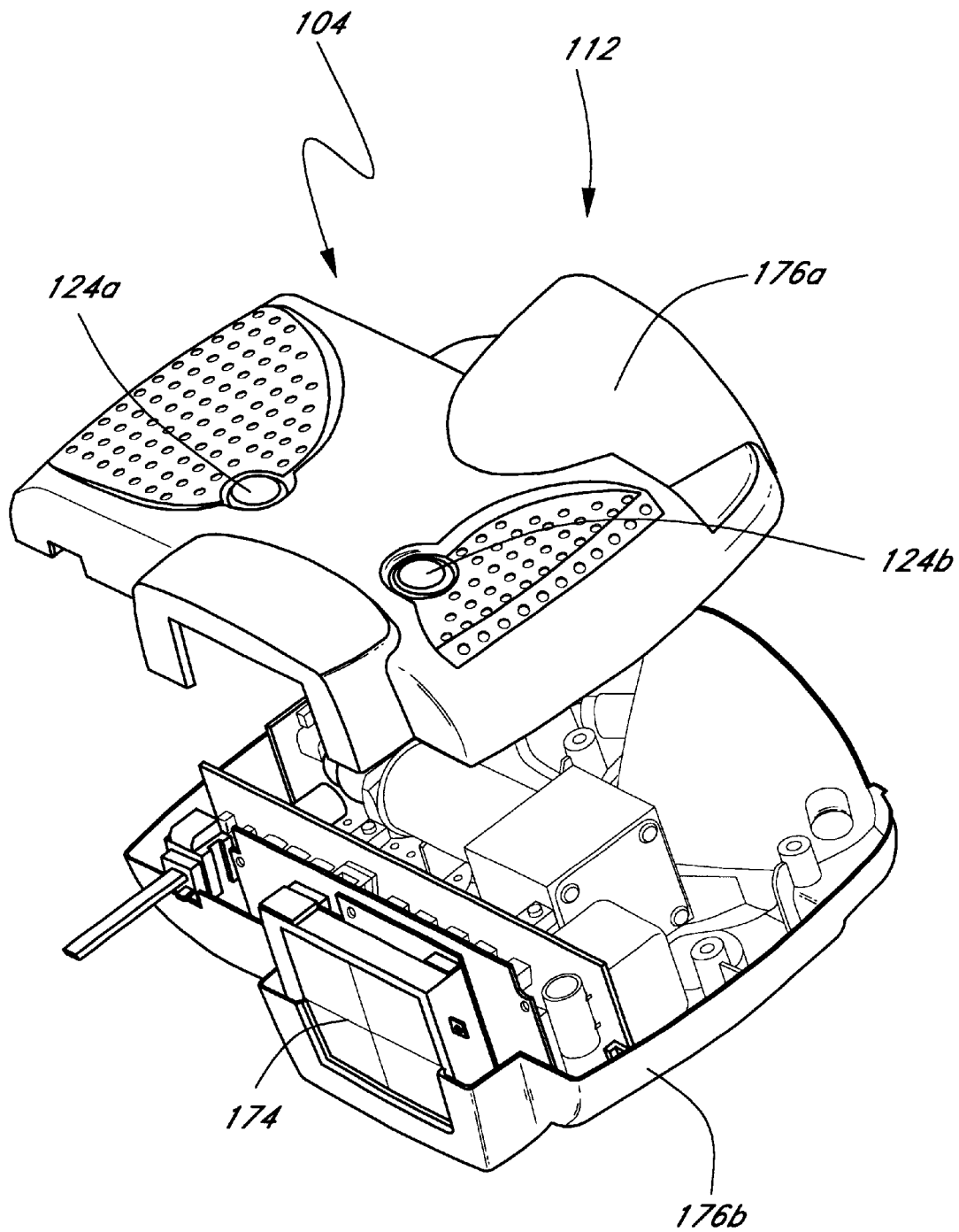
FIG. 3C is a perspective view of the handheld unit with the cover partially removed, taken from a second perspective to further illustrate the components of the handheld unit.

As shown in FIG. 3C, the LCD display 114 is in this embodiment located so that the LCD display 114 is centered about the axis of the placido projector 112. As will be described in greater detail below in reference to FIG. 11, the LCD display 114 includes cross-hairs 174a and 174b that are preferably centered on the axis 135 of the placido projector 112. The operator when viewing the placido image reflected off of the patient's cornea 150, can generally align the axis 135 of the placido projector 112 with the optical axis 152 by centering the cross-hairs 174 at the center of the innermost reflected mire 130. The center of the innermost reflected mire generally corresponds with the apex 154 of the patient's cornea 150. Hence, the handheld unit 104 is preferably constructed so that the alignment of the axis 135 of the placido projector 112 with the optical axis 152 of the patient's cornea 150 can be achieved by the operator aligning the cross-hairs 174 with the center of the innermost mire 130 in the reflected image displayed in the LCD display 140. The operator then moves the handheld unit 104 back and forth along the optical axis 152, while keeping the cross-hairs 174 centered until the quadrature detector 164 detects that the light from the laser 156 is reflecting off of the apex 154 of the patient's cornea. At which point the cornea topography system 100 shuts off the laser 156 and institutes a frame grabbing operation whereby the reflected image of the placido mires at the point of alignment of the handheld unit 104 is captured. In this embodiment, the LCD is comprised of a 2½ inch screen size LCD having a 51.3 mm×37 mm viewing area, such as the LCD display available from Tri-M Systems Inc. of Coquitlam B.C., Canada.

As is further illustrated by FIGS. 3A and 3C, the handheld unit 104 is comprised of two, preferably plastic, shell members 176a and 176b that define a recess 180 for the placido projector 112 and the light source 146 with the recess 180 being seized to receive the light panel 146 and the placido projector 146 while being retained within the recess by a lip 182 that extends around an outer surface 184 of the placido projector 112. Similarly, as shown in FIG. 3C the shell member 176a and 176b also define a recess 186 for the LCD display 114 that is seized so as to retain the LCD display 114 and its desired orientation with respect to the axis 135 of the placido projector 112.

Figure 4A:
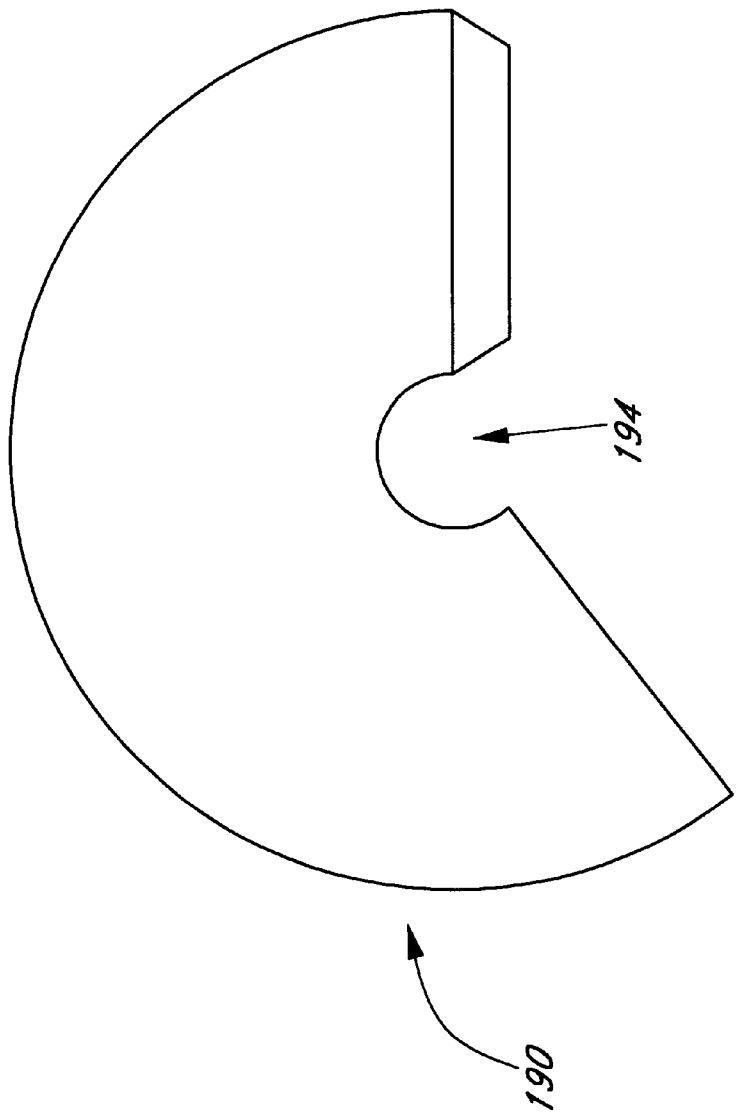
FIGS. 4A and 4B are illustrations illustrating the configuration of the light tape which provides a light source for the handheld unit of the corneal topography system of FIG. 1.
Figure 4B:
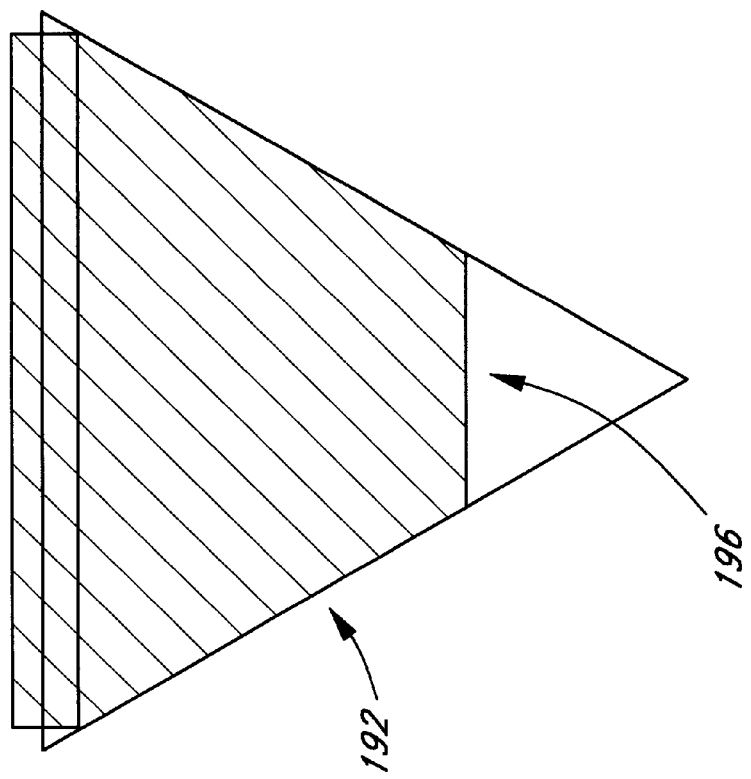

FIG. 4A and 4B illustrate the configuration of the EL panel 190 comprising the light source 146 in greater detail. Specifically, as illustrated in FIG. 4A, the light source 146 is comprise of an EL panel 190 that is cut into a half circle that can be folded together to form the frusto conical shape 192 shown in FIG. 4B. As will discussed in greater detail below, the outer surface of the placido projector 112 in this embodiment is also frusto conical. Hence, the EL panel 190 includes a cut-out 194 that is sized so that when the EL panel 190 is folded into the frusto conical shape 192, an opening 196 is formed. The opening 196 corresponds to the opening 132 (FIG. 3A) in the placido projector 112 which is positioned along the axis 135 of the placido projector 112 to thereby allow the reflected image of the placido to be received by the camera 140 in the manner described above.

The EL panel 190 is made of a thin flexible material that can be secured into the frusto conical shape 192 through the use of tape or any other suitable adhesive. In this embodiment, the EL panel 190 includes a voltage regulator that is supplied by the manufacturer. The voltage regulator receives a low voltage signal from the handheld unit's 104 power regulators and converts this into a high voltage, high frequency signal that results in the EL panel uniformly luminescing.

Figure 5A:
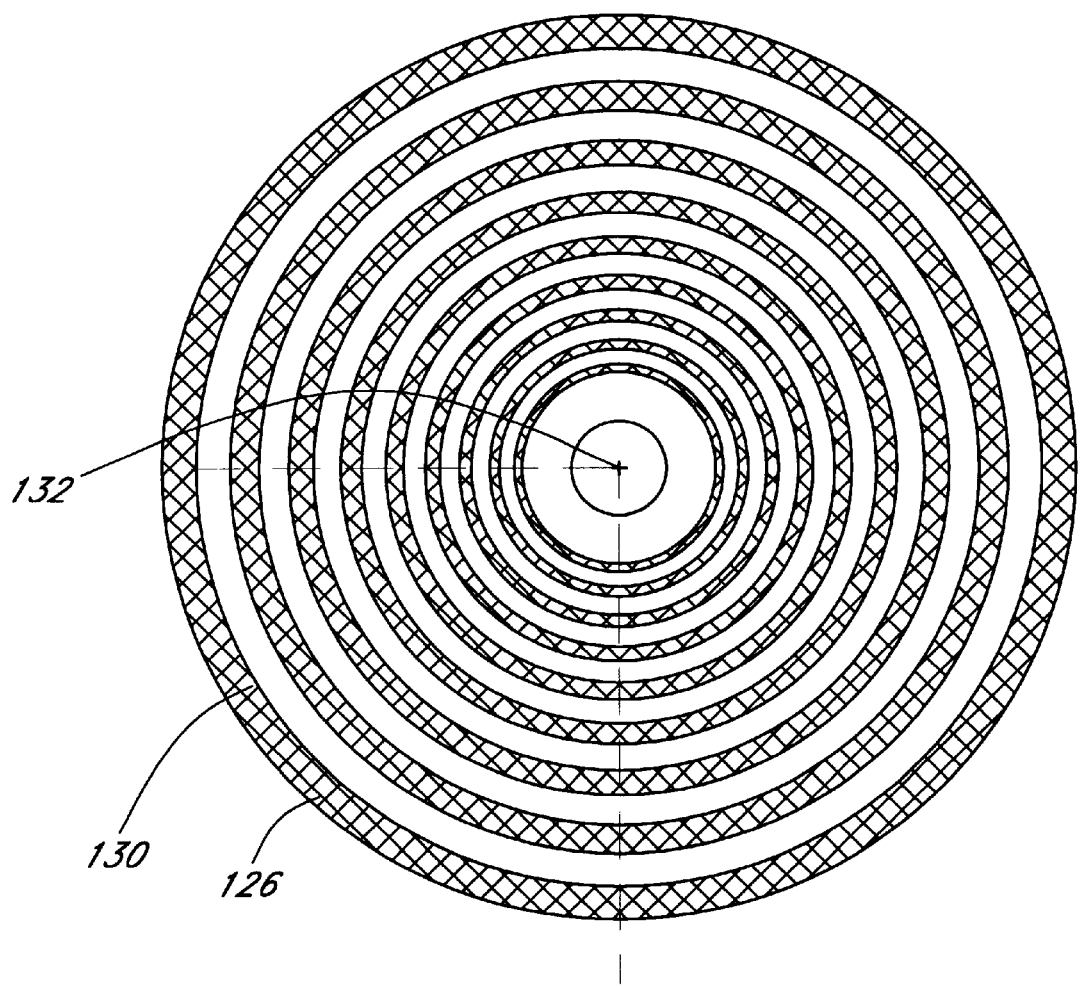
FIGS. 5A and 5B are illustrations illustrating the configuration of the placido projector incorporated into the handheld unit of the corneal topography system of FIG. 1.
Figure 5B:
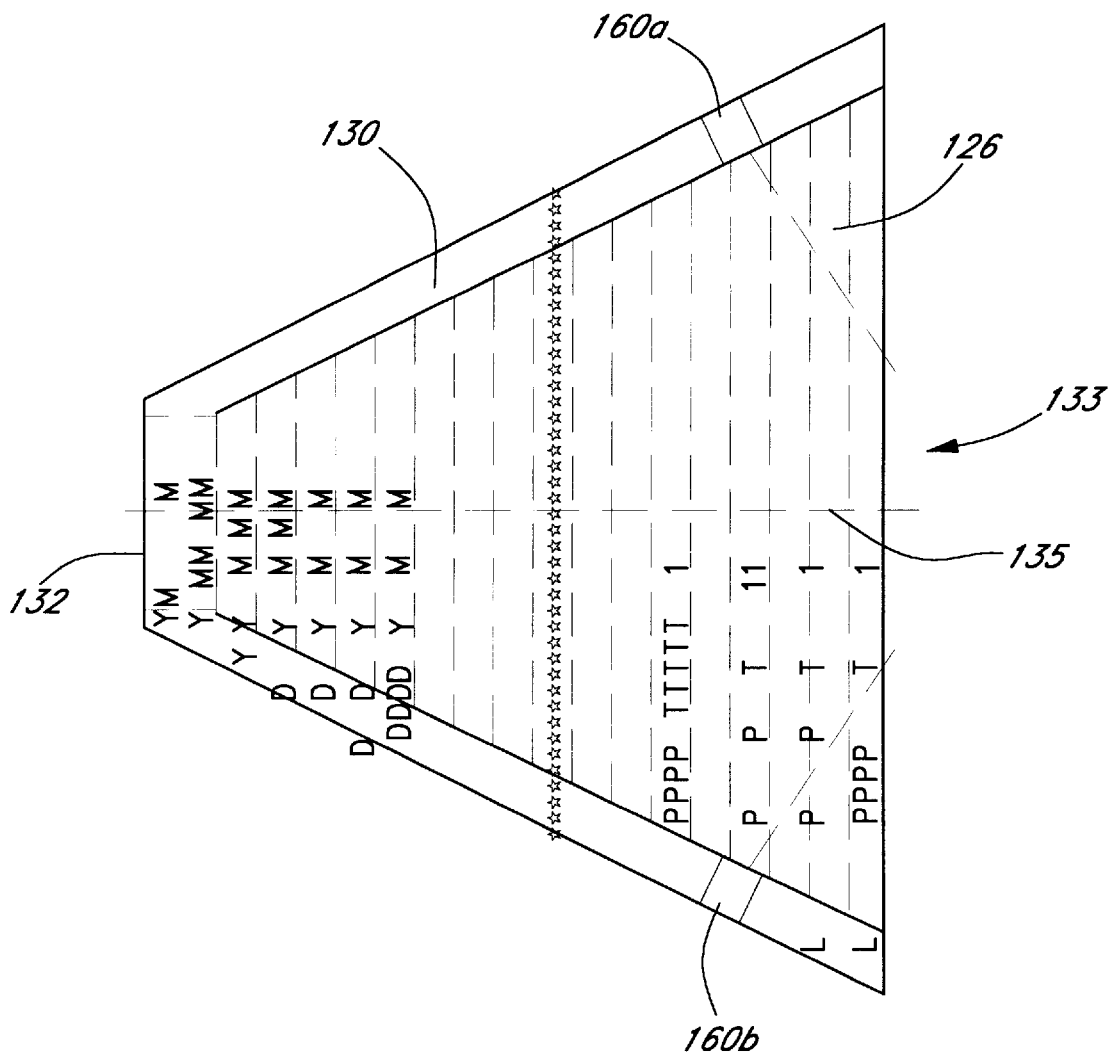

Referring now to FIGS. 5A and 5B, the placido projector 112 will now be described in greater detail. As discussed above, the placido projector 112 is made of a translucent material, such as plastic, and has a plurality of concentric mires 130 painted on the inner surface 126 of the cavity 124. As shown in FIG. 5B the outer surface 200 of the placido projector 112 is generally frusto conical in shape. This allows the EL panel 190 which comprises the light source 146 in this embodiment to be positioned immediately adjacent the outer surface 200 of the placido projector 112 so as to uniformly illuminate the placido projector 112 to thereby produce the placido image that is to be reflected off of the cornea 150 of the patient.

Preferably, the EL panel 190 is made of a material that is sufficiently flexible to be folded so as to be continuously in contact with the entire outer surface 200 of the placido projector 112. As discussed above, the inner surfaces 126 of the placido projector 112 defines a cavity 126. In this embodiment, the inner surfaces 126 are curved so as to be elliptical in shape and the plurality of concentric mires 130 are formed on the elliptical inner surfaces 126 so as to define the pattern shown in FIG. 5A. Specifically, in FIG. 5A, there are a plurality of nine concentric opaque rings 130 that are formed on the elliptical inner surfaces 126 that are positioned so as to be centered about the center point of the circular opening 132 in the placido projector 112. The nine concentric opaque rings 130 are separated by corresponding translucent rings 133. As will be discussed below, the edges between the opaque rings 130 and the translucent rings 133 provide the data points for the corneal topography analysis. Hence, in this embodiment, there can be as many as 18 rings where data will be obtained for the corneal topography analysis. As discussed above, the circular opening 132 provides an opening for the image of the mires reflected off of the patient's cornea 150 to be passed to the prism 134 and then to the CCD camera 140.

As is also shown in FIG. 5B, two openings 160a and 160b are formed through the placido projector 112 that are positioned and angled so as to allow the laser 156 and the quad detector 162 to perform the Z-axis positioning function that was described above. In this preferred embodiment, the placido projector 112 is approximately two inches long, i.e. two inches from the inner opening 132 and the outer opening 133 and the outer surface of the placido projector 200 extends outward from the axis 135 of the placido projector 112 at approximately a 37 degree angle. The inner opening 132 is on the order of one half of an inch in diameter.

From the foregoing it will be appreciated that the placido projector 112 is particularly compact in size which reduces the overall size and weight of the handheld unit 104. Moreover, the use of the EL panel 190 as the light source 114 further reduces the overall size and weight of the handheld unit 112. The reduction of size and weight of the handheld unit 104 allows the operator to more accurately locate the handheld unit 104 in the desired orientation with respect to the patient's cornea 150 by hand. The small and lightweight placido projector and light source thereby facilitate the use of the handheld unit 104 which eliminates the need for a large and expensive system for moving and orienting the placido projector with respect to the patient's cornea to obtain corneal topography data.

Figure 6:
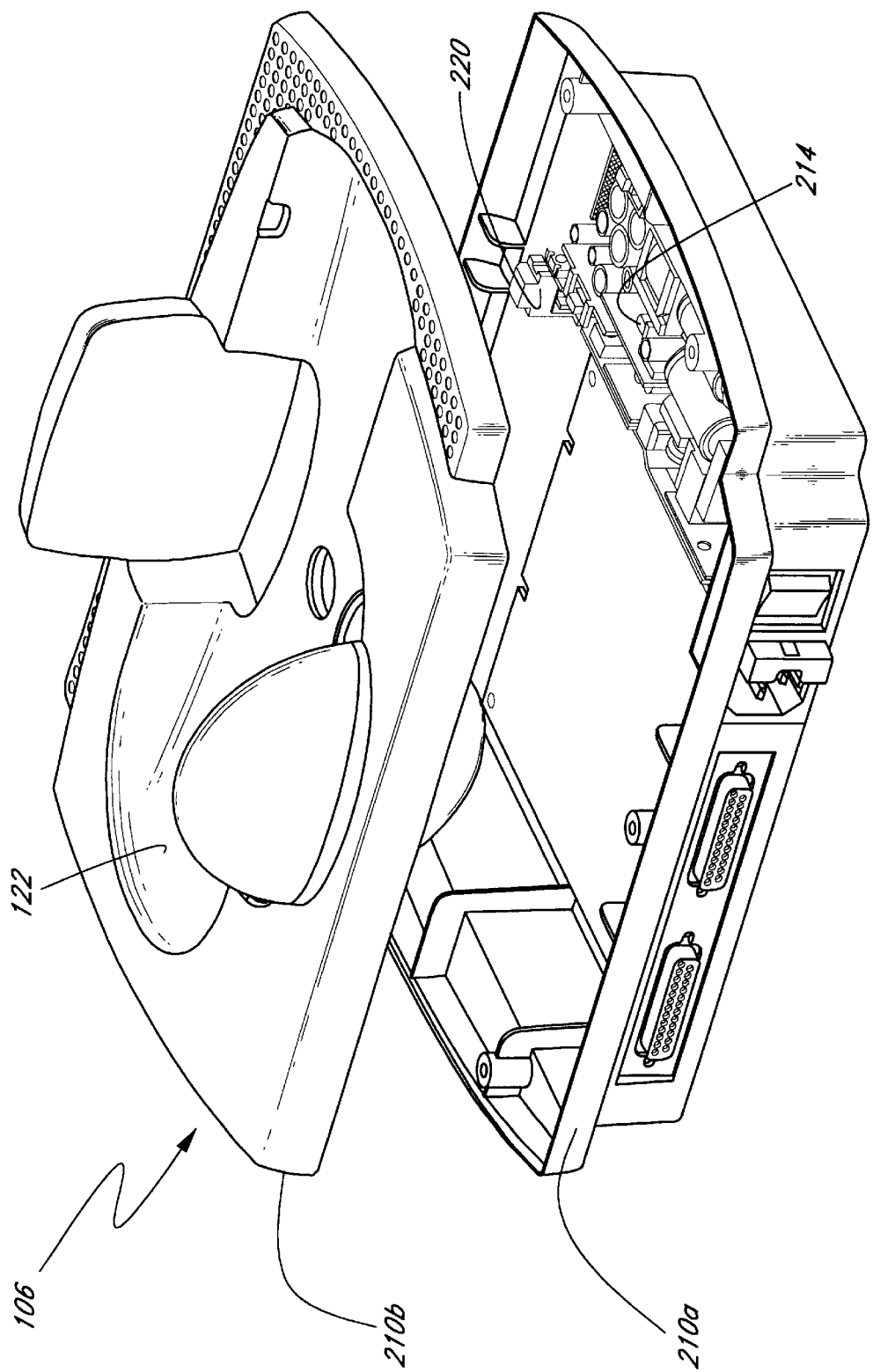
FIG. 6 is a perspective view of a base unit that includes a cradle for the handheld member with the cover partially removed so as to illustrate the components of the base unit.

The base unit 106 will now be described in reference to FIG. 6. As shown in FIG. 6, the base unit 106 is comprised of two shells 210a and 210b that define a cavity 212 which contains electronics 214 that will be described in greater detail in reference to FIG. 8. As discussed above, the base member 106 defines a receptacle 122 which is sized so as to receive the handheld unit 104 when the handheld unit 104 is not in use. Moreover, the base member 106 also includes to parallel port computer connection pins 216a and 216b which allow the base unit 106 to communicate with the personal computer 102 in a manner that will be described in greater detail below. Further, the base unit 106 also include a serial-type connection port 220 that allows the base unit 106 to communicate with the handheld unit 102 by the serial-type interface 125 in a manner that will be described in greater detail below. The base member 106 in this embodiment also preferably include a power input 222 and an on/off switch 224. Power for the components of the base member 106 and the handheld unit 104 is provided to the base member 106 by the power input 222 and the on/off switch 224. In this embodiment, the base member 106 is adapted to use standard power (120–230 Volts) and has appropriate regulation circuitry to provide the necessary power to the components of the base member 106 and the handheld unit 104.

Figure 7:
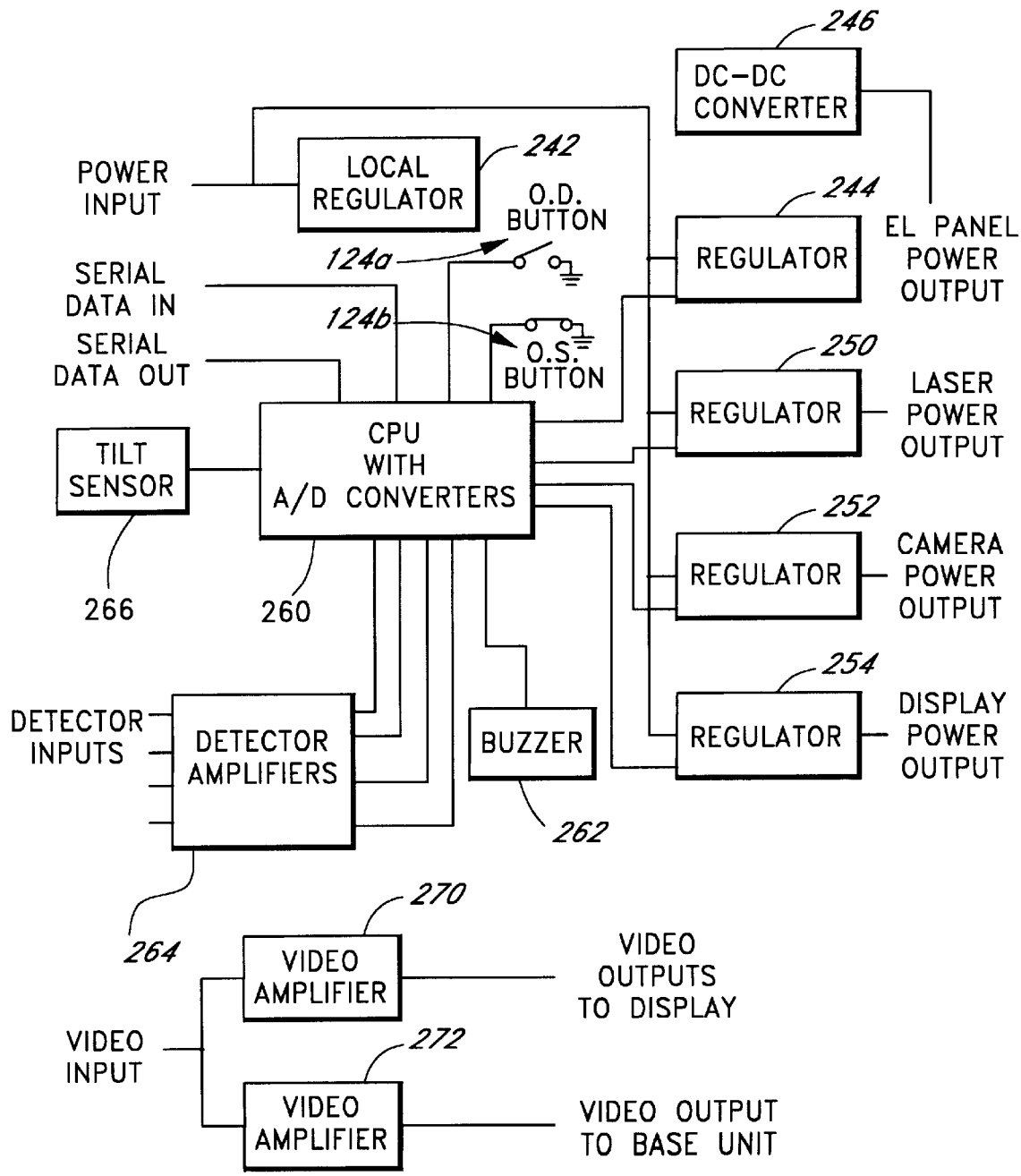
FIG. 7 is a functional block diagram which illustrates the functional components of the handheld unit of FIGS. 3A–3C.

FIG. 7 is a functional block diagram which illustrates the functional components of the handheld unit 104. The handheld unit 104 receives power by a power input through the interface 125. The power input is provided to a local regulator 242 which powers the components of the handheld unit 104. Further, the power input is also provided to a regulator 244 for the EL panel 190 which is the light source in this embodiment. The regulator 244 is connected to the EL panel 190 by a DC to DC converter 246 that is selected so as to provide the appropriate input power to the EL panel to have the EL panel luminous in the above described fashion. The power input is also provided to a regulator 250 for the laser 156, a regulator 252 for the CCD camera 140 and a regulator 256 for the LCD display 114.

Each of the regulators 244, 250, 252 and 254 also receive an input from a processor or CPU 260 so that the processor 260 can turn on and off the EL panel 190, the laser 156, the CCD camera 140 and the display 114 in a manner that will be described in greater detail below. The processor 260 also provides and output signal to a buzzer 262. The CPU 260 enables the buzzer 262 to signal to the operator when the handheld unit 104 is ready to obtain an image. The processor 260 also receives series of inputs including inputs from the buttons 124a and 124b positioned on the top of the handheld unit 102. The buttons 124 provide the processor 260 with an indication as to which eye the operator is intending to take a picture of and this information is sent to the computer 102 via the base unit 106 by the serial interface 125 on the serial data outline. The processor 260 also receives signals from the quadrature detector 164 to enable processor 260 to determine whether the handheld unit 102 is correctly located along the optical axis 152 in the above-described manner.

The processor 260, in this embodiment, also receives input from a tilt sensor 266 that is mounted within the handheld unit 104. The tilt sensor 266 is preferably a solid state tilt sensor such as a DXL-05 tilt sensor available from Analog Devices, Inc. of Norwood, Mass. As will be discussed in greater below, the processor 260 provides a signal to the computer 102 after the reflected image has been captured indicative of the tilt of the handheld unit 104 at the time of capture. It will be appreciated that if the handheld unit was tilted about the optical axis 152 so as to be out of range, the resulting captured image may not directly correspond to the calibration data thereby resulting in poor corneal topography data.

As is also shown in FIG. 7, the video input from the camera 140 is provided to a video amplifier 270 which provides video output to the LCD display 114. Similarly, the camera 140 also provides a signal to a video amplifier 272 that provides video output to the base unit 106 via the interface 125 in a manner that will be described in greater detail below. Hence, the handheld unit 104 includes a processor 260 that controls the operation of the components of the handheld unit 104. Moreover, input signals are also provided to the processor 260 by the interface 125 so as to control the operation of the handheld unit 104 in a manner that will be described in greater detail below.

Figure 8:
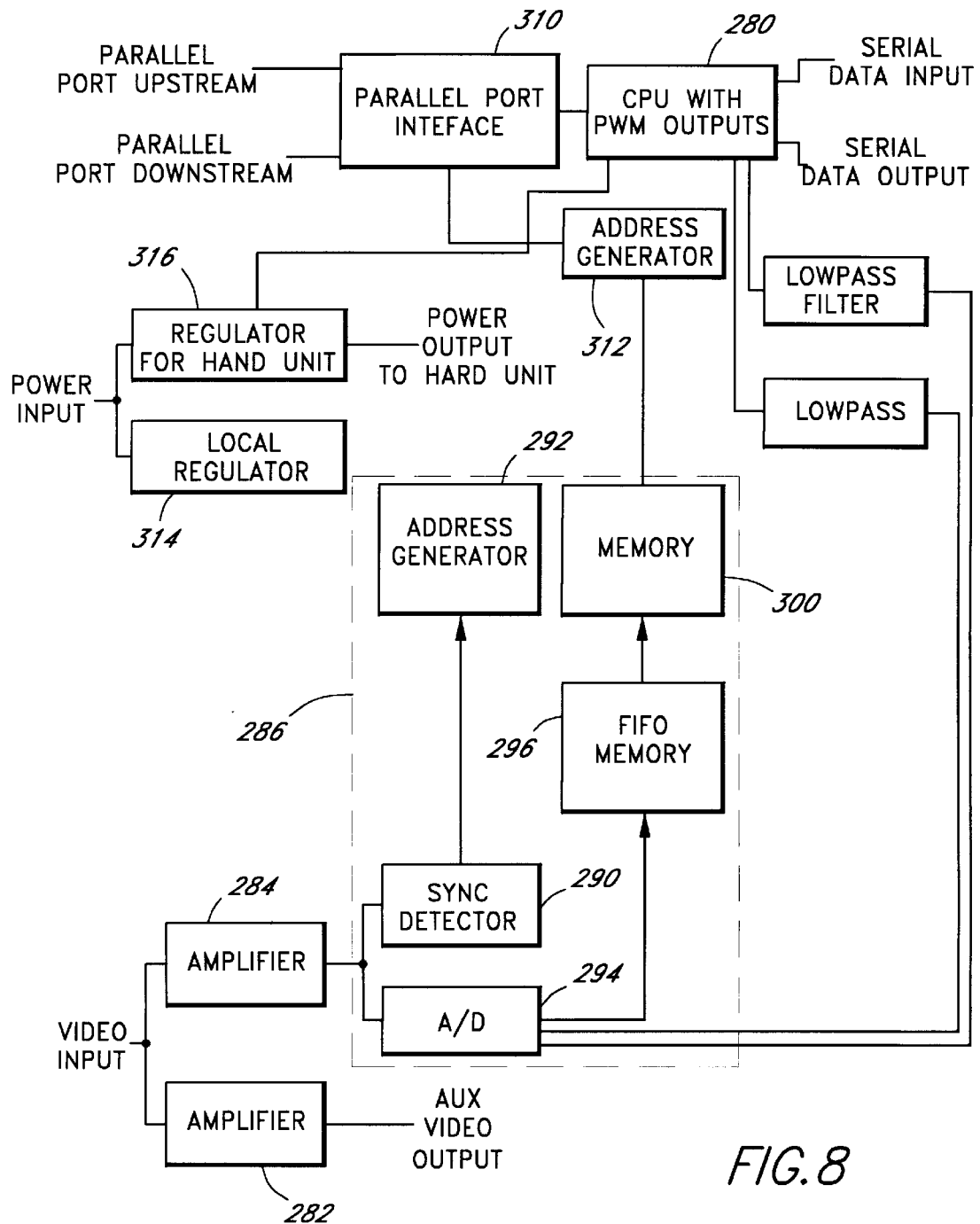
FIG. 8 is a functional block diagram illustrating the functional components of the base unit of FIG. 6.

FIG. 8 is a functional blocked diagram which illustrates the components of the base unit 106. The base unit 106 includes a CPU or processor 280 that receives serial data from the handheld unit 104 by the serial interface 125. Similarly, the processor 280 also provides serial data to the handheld unit 104 by the serial interface 125. Specifically, the processor 280 receives signals from the processor 260 of the handheld unit 104 when the processor 260 has ascertain that the operator has initiated the sequence by depressing one of the buttons 124a or 124b or when the processor 260 has received signals from the quadrature detector 162 that the handheld unit 104 is in the correct orientation with respect to the patient's cornea 150.

The base unit 106 also receives a video input over the interface 125 from the handheld unit via the video amplifier 270 (FIG. 7). The video input signal received by the base unit 106 is split so that one signal is provided via an amplifier 282 to an auxiliary video output. The auxiliary video output allows a technician or assembler to plug a video display into the output so as to be able to observe the signal being received from the handheld unit 104. The video input signal is also provided via an amplifier 284 to a frame grabber 286 that is adapted to store the frame of video data that corresponded to the moment the handheld processor 260 determines the handheld unit 104 was in the proper orientation with the patient's cornea. The frame grabber 286 includes a synch detector 290, an address generator 292 which generates address for the stored frame and an A to D converter 294 which converts the incoming analog video signal into a digital signal. The A to D converter provides the digital signal to a FIFO memory 296 which operates as a buffer. The frame grabber 286 also includes a memory 300 which will receive and store the digital data from the FIFO memory 296 that corresponds to the frame that is to be grabbed.

Basically, the handheld unit 104 continuously provides a video signal via a video link to the base unit 106. The processor 280 of the base unit 106 is also in contact with the processor 260 of the handheld unit 104 so that when the processor 260 receives a signal from the quadrature detector 264 indicating that the handheld unit 104 was in the proper orientation with the patient's cornea 150, the processor 280 receives an appropriate signal from the processor 260 so that a frame of the video input signal that corresponds to the moment of proper orientation is stored in the memory 300. In this embodiment, the stored frame is selected so as to correspond to the video frame that was being received by the CCD camera 140 at the time that the quadrature detectors 164 determined that the handheld unit 104 was in proper alignment with respect to the patient's cornea 150. The operation of the frame grabber 286 is similar to the operation of any of a number of well-known configurations of frame grabbers that receive a continuous video signal and, upon a occurrence of a particular condition, record a particular frame of the incoming video signal in a memory.

The base unit 106 also includes a parallel port interface 310 that communicates with the computer 102 via the parallel ports 216a and 216b (FIG. 6). The computer 102 can then access and download the frame that is stored in the memory 300 via the parallel port interface 310 and an address generator 312. This allows the personal computer 102 to access and download the stored frame so that the stored frame can be furthered process to obtain the corneal topography data in a manner that will be described in greater detail below.

As is also illustrated in FIG. 8, the base unit receives power by the power input (FIG. 6) which is then provided to a local regulator 314 which then provides the appropriate power to each of the components of the base unit 106. Similarly, the power for the handheld unit 104 is provided by the base unit 106 by a regulator 316. In this manner, power can be provided to the handheld unit 104 via the interface 125 while leaving some of the power regulation components in the base unit 106 to thereby decrease the overall weight of the handheld unit 104.

Figure 9:
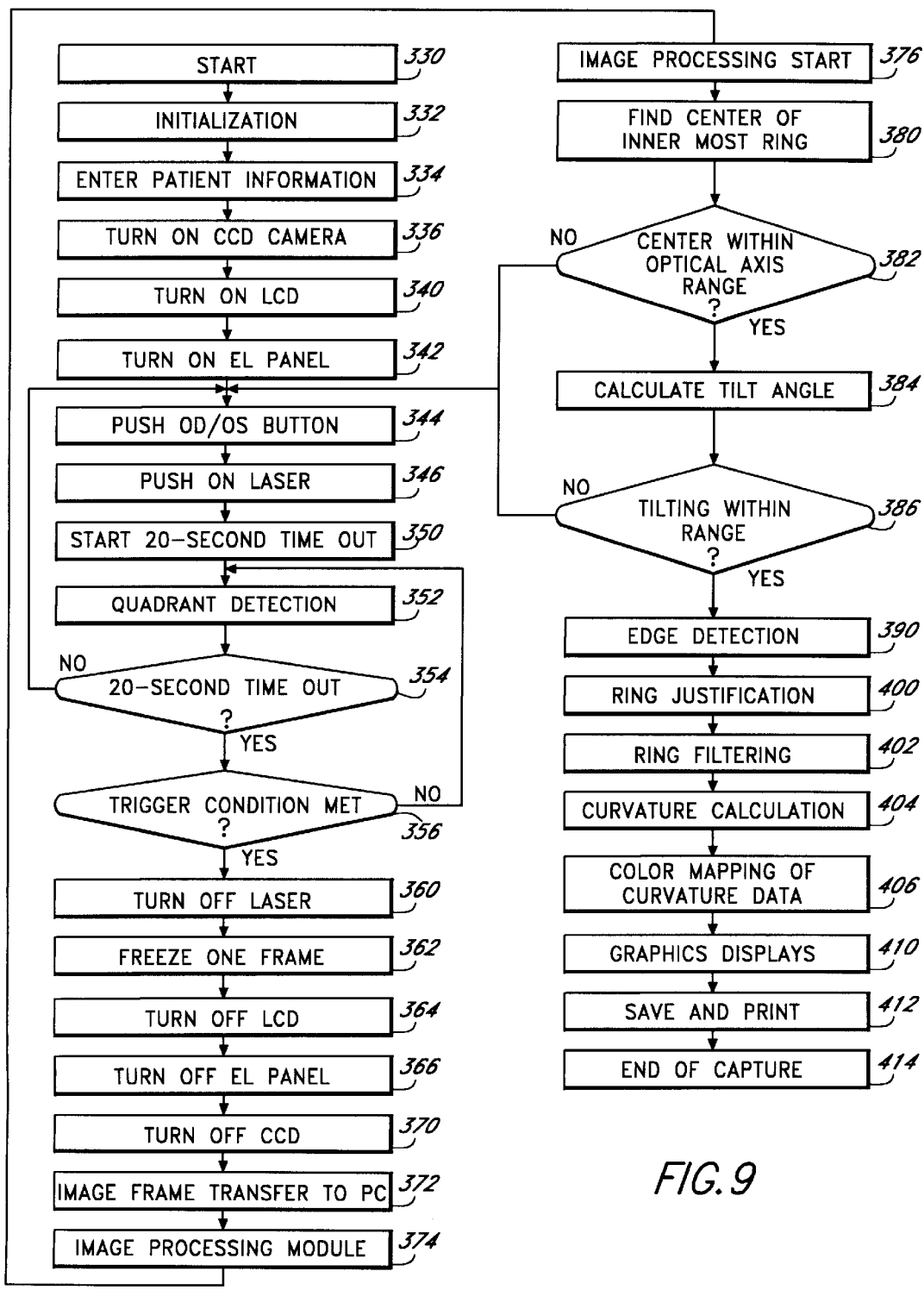
FIG. 9 is a flow chart illustrating the functional operation of the corneal topography system of FIG. 1 as it implements a process whereby an image of the patient's eye is captured and the data is subsequently verified and then analyzed to obtain the corneal topography data.

The operation of the system 100 will now be described in reference to the flow chart of FIG. 9. The computer 102 generally controls the overall operation of the system 100 by sending appropriate commands to the handheld unit 104 and the base unit 106. The personal computer 102 takes the image obtained by the handheld unit 104 and captured by the base unit 106 and then performs well known corneal topography analysis techniques wherein the position of the mires on the resulting image are compared to calibration data so that the topography of the cornea 150 can be determined from the resulting image. The operation of the system 100 will now be described in greater detail in reference to the flow chart of FIG. 9.

Initially, from a start state 330, the computer 102 initialized the system 100 in state 332. The initialization step incorporates such things as booting up the computer 102, initializing the processors in the base unit 106 and the handheld unit 104 and similar functions. Once the system has been initialized, the operator then enters patient information in state 334 into the computer 102 via the keyboard 110 and mouse 120 (FIG. 1). This information can, for example, include such things as personal information, results of other tests etc. and all of this information can be stored in a memory device associated with the computer. Once the appropriate patient information is entered, the cycle of obtaining the corneal topography data can then be initiated.

Specifically, the computer 102 sends an appropriate signal to the handheld unit 104 to enable the varies components of the handheld unit 104. In particular, the CCD camera 140 is turn on in state 336, the LCD display 114 is turned on in state 340 and the EL panel 190 which comprises the light source 146 is turned on in state 342. At this point, the handheld unit 104 is operating in the sense that the placido projector 112 is projecting a placido image and the resulting reflected images being captured by the CCD camera 140 is provided to the LCD display 114 on the handheld unit 104. This allows the operator to begin to attempt alignment of the handheld unit 104 with respect to the cornea 150 of the patient.

At this point, the patient will push one of the buttons 124a or 124b in state 344 to signal to the computer 102 the eye from which the reflective image is to be captured. The computer 102 records this information in a record in the memory of the computer corresponding to the particular patient so that the resulting corneal topography imaging data can stored in an appropriately identified data structure. Further, once the button 124a or 124b has been depressed, the processor 260 of the handheld unit 104 turns the laser 156 on so as to begin the process whereby the processor 260 will ascertain whether the handheld unit 104 is appropriately aligned or oriented with respect to the patient's cornea 150.

Specifically, as discussed above, the operator is looking into the LCD display 114 and is viewing an image of the patient's cornea with the placido mires 130 reflecting therefrom. An exemplary image as seen by the operator in the LCD display 114 is reproduced in FIG. 11 below. As shown, the LCD display 114 includes cross-hairs 170a and 170b that are physically formed on the LCD display 114 so that alignment of the cross-hairs 170 on the image displayed on the LCD display 114 results in a corresponding alignment of the axis 135 of the placido projector 112 and the optical axis 152 of the patient's eye.

It is understood that the center of the patient's cornea is almost always spherical in shape and any deformation of the curvature of the cornea is less likely to occur at the location of the centermost mire 131'. Consequently, it is understood that the innermost mire 131' for most patients' corneas is likely to be very circular and that the center point of the centermost mire 131' is likely to correspond to the apex 154 of the patient's cornea 150. Moreover, it is also understood that as the cornea 150 of even a patient with a badly deformed cornea will still be somewhat spherical, the resulting reflected image of the innermost mire will still be generally centered about the apex 154 of the cornea 150.

Hence, the operator can align the axis 135 of the placido projector with the optical axis 152 of the patient's cornea 150 that extends out of the apex 154 of the patient's cornea 150 by centering the cross-hairs 170a and 170b at the center of the innermost opaque mire 131'. It is well understood phenomenon that the human eye is particularly adapted to finding the center of the circle. Consequently, the operator can fairly precisely locate the cross-hairs 170a and 170b in the center of the image of the innermost reflected mire 131' as displayed in the LCD display 114 with some degree of precision which results in a fairly close alignment between the axis 135 of the placido projector 112 and the optical axis 152.

Once the operator has appropriately aligned the placido axis 135 with the optical axis 152, the operator then begins to move the handheld unit 104 along the optical axis 152 while the laser 156 is beaming a light beam at the patient's cornea 150. As discussed above, the laser 156 and the quadrature detector 162 are preferably positioned so that the laser 156 will preferably reflect off of the apex 154 of the patient's eye resulting in the quadrature detector 164 obtaining a uniformly distributed light beam when the handheld unit 104 is appropriately spaced along the optical access 152 from the apex 154 of the patient's cornea 150. Preferably, the laser 156 projects a non-visible medically safe beam on the cornea 150 so it does not hurt the patient or cause the patient to blink.

Returning to FIG. 9, once the laser 156 is turned on in state 346, the processor 260 begins a twenty second timer in a state 350 and then also begins to analyze the signals provided by the quadrature detector 162 in a state 352. If the timer times out in twenty seconds the operator must re-initiate the image captured function by pushing the buttons 124a or 124b in state 344. If the time out period has not been met, the processor 260 then ascertains whether the signals provided by the quad detector 162 meet the trigger conditions in decision state 356.

In one embodiment, the trigger conditions will be met only when all four of the quadrants of the quadrature detector 156 receive an equal distribution of light. As discussed above, the laser 156 and the quadrature detector 164 are located so that this condition only occurs when the handheld unit 104 is spaced from the apex 154 of the cornea 150 a known distance such that the laser 156 is incident on the apex 154 and the beam is being reflected from the apex 154 to the quadrature detector 154.

Figure 10:
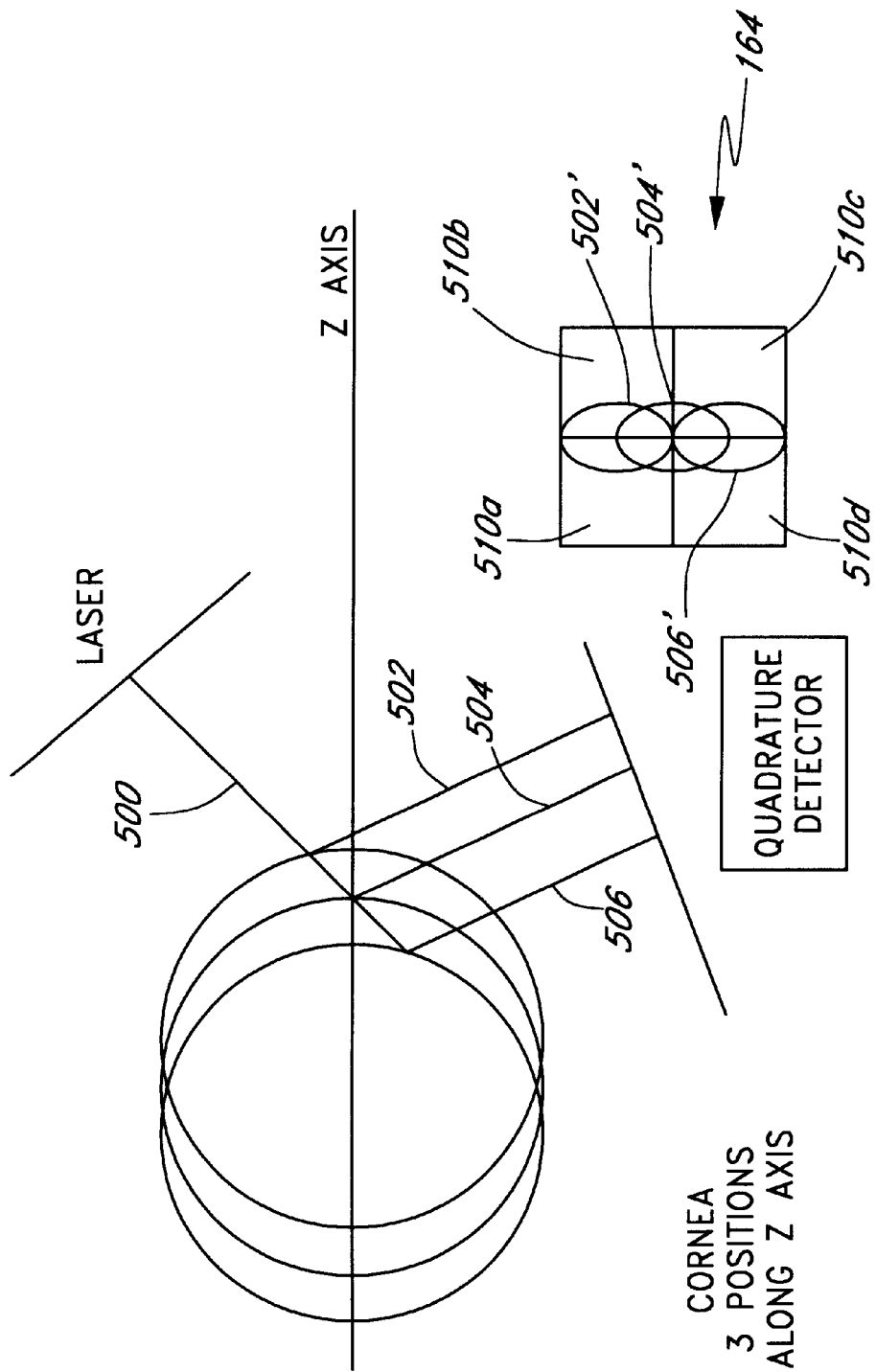
FIG. 10 is a schematic illustration which illustrates the operation of the automatic normal axis positioning system of the handheld unit of the corneal topography system of FIG. 1.

FIG. 10 is a schematic illustration illustrating the operation of the laser 156 in the quadrature detector 164 when a laser beam 500 is being reflected off of the cornea 150. The cornea 150 in FIG. 10 is illustratively shown as being located at three positions along the Z-axis or the optical axis 152. If the handheld unit 104 is too close to the eye, the reflected beam 502 will not be uniformly distributed across all four quadrants 510a–510d of the quadrature detector 164. Similarly, if the handheld unit 104 is positioned to far from the cornea 150, the resulting reflected beam 506 will also not be uniformly distributed across all four quadrants 510a–510d 510D. Only when the handheld unit 104 is the exact desired distance along the Z-axis from the apex 154 of the cornea 150 will be resulting reflective beam 504' be distributed evenly across all four of the quadrants 510a–510d. This is the trigger condition of the preferred embodiment which, if met, results in the processor 260 turning off the laser in state 360 and initiate a process whereby one frame is frozen in state 362.

The freeze frame function 363 is performed by the processor 280 of the base unit 106 using the frame grabber 286 in the above described manner. In this fashion, the frame of the video signal that corresponds to the moment of alignment between the handheld unit 104 and the cornea 150 is captured and stored in the memory 300 of the frame grabber 286.

The processor 260 of the handheld unit then turns off the LCD in state 364, turns off the light source in state 366 and turns off the camera in state 370. Subsequently, the image stored in the memory 300 (FIG. 8) of the frame grabber 286 can then be transferred to the personal computer 102 in a state 372 via the parallel port interface 310. An image processing module 374 comprised of the states 376 through 414 can then be initiated by the personal computer 102.

Specifically, from a start state 376, the computer 102 mathematically locates the center of the innermost reflective mire 131 ' (FIG. 11) in state 380. The location of the center of the innermost reflective mire 131' is performed using a well known algorithm. Once the center of the innermost mire 131' is located, the processor then determines in decision state 382 whether the center is within the optical access range. Specifically, the centermost pixel of the captured reflected image can be ascertained by the computer 102. The handheld unit 104 is preferably constructed so that the centermost pixel of the captured image corresponds to the location of the image that was positioned on the axis 135 of the placido projector 112 when the image was captured. This location can then be compared to the mathematically calculated center of the innermost mire 131' to ascertain whether these two locations are sufficiently close so that the captured image would provide accurate corneal topography data.

If these two locations are not sufficiently close, the computer 102 sends an appropriate signal to the operator via the computer's display 116 to retake the image. If, however, the computer 102 determines in decision state 382 that the center of the innermost mire 131' is within the optical access range, the computer 102 then proceeds to calculate the tilt angle of the handheld unit 102 in state 384 at the time of capture of the reflective image.

As discussed above, the handheld unit 104 incorporates a tilt sensor that provides a continuous signal to the processor 260 indicative of the angle of tilt of the handheld unit 102. If the handheld unit 102 was tilted or rotated too much about the optical access 152, the resulting corneal topography data may be inaccurate. In one embodiment, the tilt angle will not be within range if it is greater than 5 degrees tilt. In another embodiment, algorithms can be implemented that will correct the data if the tilt angle is between 5 and 15 degrees and will ignore any tilt angle that is less than 5 degrees of tilt. The processor 260 is configured, so that upon the triggering of the frame grabbing sequence, the tilt angle at that moment is stored and is subsequently downloaded to the computer 102. The computer 102 then ascertains whether the tilt angle is within acceptable tolerances to yield accurate data. If the tilt angle is not within range, an appropriate signal is provided to the operator via the display 116 of the computer 102 to re-initiate the image capture sequence at state 344.

If the tilt angle was within range, and the calculated center of the reflective image was within the optical range then the captured image of the reflective mires is presumed to yield sufficiently accurate corneal topography data. Consequently, the computer 102 at that point then begins to compare the X and Y locations of each of the reflected mires 130' (FIG. 11) to the corresponding X and Y positions of a corresponding mire on a calibration sphere. Specifically, calibration data is stored within a data structure in the memory of the computer 102. This calibration data is essentially the X and Y locations of the mires of the same placido image reflected off a perfect calibration sphere in a corresponding orientation with respect to the handheld unit 104. This allows for a comparison between the X and Y locations of the mires on the image reflected from the patient's cornea and the X and Y locations of the calibration mires. This comparison can yield the degree of deviation of the curvature of the patient's cornea 150 from the calibration spheres and this yield the corneal topography of the patient's cornea. These calculations are performed using well known algorithms and well known calibration models.

Specifically, in this embodiment, the computer 102 initially proceeds to perform an edge detection algorithm in state 390 on the reflected image. This edge detection algorithm detects the X and Y locations of each of the edges and reflected mires 130' and 131' (FIG. 10). Subsequently, the computer 102 performs various justifications and filtering algorithms in state 402 so that a curvature calculation can be performed in state 404 for a plurality of points along each of the edges of the reflected mires 130' and 131'. As discussed above, this curvature calculation is performed by comparing the resulting X,Y coordinates of the edges of the mires to corresponding coordinates on corresponding mires as obtained using calibrations spheres.

The curvature calculations of state 404 yield curvature data which can then be used to color map the image in state 406. This color map image can then be displayed on the display 116 in a state 410 and this image can also be saved to the computer's memory and also printed in state 412 thereby ending the captured data sequence in state 414. The algorithms used to obtain the corneal topography data and also to develop a color printed maps are substantially similar to the algorithms used, for example, by Eyesys Technologies, Inc. formerly of Houston, Tex. and now of Irvine, Calif. in their Model 2, Model 3 and System 2000 products.

From the foregoing, it will be apparent that the handheld corneal topography provides a unique system for capturing an image of mires reflecting off of the cornea of the patient and also for ascertaining that the image will yield valid data. As the handheld unit incorporates a light weight light source and placido projector and further incorporates detectors which will detect correct orientation between the apex of the cornea and the handheld unit, a simpler more compact portable device can be used to obtain accurate corneal topography data. This results in less space in the ophthalmologist office being occupied by a corneal topography machine and further increases of flexibility of use in patient care using the corneal topography system of the preferred embodiment.

Although the foregoing description of the preferred embodiment of the present invention has shown, described and pointed out the fundamental novel features of the invention it will be understood that various omissions, substitutions and changes in the form of the detail of the apparatus as illustrated as well as the uses thereof, maybe made by those skilled in the art without departing from the spirit of the present invention. Consequently, the scope of the present invention should not be limited to foregoing discussion, but should be defined by the appended claims

What is claimed is:

1. A corneal topography system comprising:
   a handheld unit incorporating a camera, a placido projector and a light source positioned within a casing that is sized so as to be movable by an operator by hand wherein the placido projector projects a placido image when the light source is illuminated and wherein the video camera obtains an image of the placido image reflecting off of a patient's cornea when the handheld unit is positioned adjacent the patient's cornea;
   an orientation alignment mechanism that is coupled to the handheld unit, wherein the orientation alignment mechanism facilitates alignment of the handheld unit with respect to the patient's cornea so that when the handheld unit is in a first relative orientation with respect to the patient's cornea, the orientation alignment mechanism provides a first signal indicative thereof; and
   an image capture system that receives (1) signals from the camera indicative of the placido image reflected from the patient's cornea and (2) the first signal from the orientation alignment mechanism wherein the image capture system, upon receiving the first signal from the orientation alignment mechanism, captures the camera signals that correspond to the moment that the handheld unit was in the first orientation with respect to the patient's cornea wherein the captured reflected placido image is indicative of the corneal topography of the patient's cornea.

2. The system of claim 1, wherein the camera is comprised of a CCD camera that sequentially provides frames of video signals to the image capture system.

3. The system of claim 1, wherein the placido projector is comprised of a generally conical translucent material having a conical outer surface, wherein the conical translucent material defines a cavity therein wherein the cavity has a plurality of opaque mires formed therein so that when the light source illuminates the placido projector, a placido image comprised; of a plurality of concentric opaque mires separated by illuminated bands is produced.

4. The system of claim 3, wherein the light source is comprised of an electro-luminescent (EL) panel that, when a voltage is applied to the panel, uniformly luminesces.

5. The system of claim 4, wherein the panel is made of a flexible material and is shaped into a conical shape so that an inner surface of the panel can be positioned immediately adjacent the outer surface of the placido projector so that when the voltage source is applied to the panel, the placido projector is uniformly illuminated.

6. The system of claim 3, wherein the conical translucent material has a first opening located at the smaller end of the conical translucent material and a second opening at the larger end of the conical translucent material and wherein the first and second openings and the cavity are positioned so as to be coaxial with a first axis extending therethrough.

7. The system of claim 6, wherein the placido projector is positioned within the handheld unit housing so that the first axis extends outward from the housing in a first direction and when the handheld unit housing is located in front of the patient's cornea, the placido image is reflected off of the patient's cornea along the axis through the first and the second opening.

8. The system of claim 7, wherein the camera is located so as to receive the placido image reflected along the first axis.

9. The system of claim 8, wherein the handheld unit also incorporates a prism that reflects the reflected placido image along a direction that is normal to the first axis and wherein the camera is mounted within the housing to receive the reflected placido image after it has been reflected by the prism along the direction that is normal to the first axis so that the overall dimension of the handheld unit in the direction of the first axis can be reduced.

10. The system of claim 9, wherein the placido projector made of a translucent plastic material that is approximately 2 inches long with the outer surfaces forming approximately a 37 degree angle with respect to the axis of the conical translucent material.

11. The system of claim 1, wherein the handheld unit also incorporates a display which also receives signals from the camera that, when the handheld unit is positioned in front of the patient's cornea, are indicative of the reflected placido image.

12. The system of claim 11, wherein the display incorporates cross hairs that, when centered on a pre-selected point on the reflected placido image being displayed on the display results in the handheld unit being positioned in a first orientation with respect to an optical axis of the patient's cornea.

13. The system of claim 12, wherein the orientation alignment mechanism includes a light source and a detector positioned in the handheld unit so that when the light source is positioned a first distance from a reference point on the patient's cornea and the handheld unit is positioned in the first orientation with respect to the optical axis of the patient's cornea, the detector receives a first reflected light beam reflected off of the reference point and produces a first detector signal thereby inducing the orientation alignment mechanism to provide the first signal to the image capture system.

14. The system of claim 1, further comprising an image analysis system that compares the relative position of the mires in the placido image reflected from the patient's cornea when the handheld unit was in the first orientation with corresponding position calibration data to determine the localized radius of curvature of the patient's cornea over a plurality of points on the patient's cornea.

15. The system of claim 14, wherein the image capture system comprises a frame grabber positioned within a base unit that is attached to the handheld unit via a flexible cord and wherein the image analysis system is comprised of a computer that is coupled to the base unit.

16. The system of claim 1, wherein the handheld unit is approximately 5¾ inches by 7¾ inches by 3½ inches and weighs less than approximately 2 pounds.

17. A corneal topography system comprising:
a handheld housing defining a first and a second axis that are orthogonal to each other and further defining a mounting cavity wherein the first axis extends through the mounting cavity;
a placido projector positioned within the mounting cavity of the handheld housing, wherein the placido projector is at least partially formed of a translucent material so as to be able to project a placido image when illuminated from a first surface and wherein the placido projector has a camera opening positioned at substantially the center of the placido projector;
a light source comprised of a flexible electro-luminescent panel that is positioned within the mounting cavity in the handheld unit so as to be interposed between the first surface of the placido projector and the mounting cavity and so as substantially cover the first surface of the placido projector, wherein the light source illuminates the placido projector to induce the placido projector to project the placido image;
a camera mounted within the housing so as to receive through the camera opening in the placido projector a reflected placido image reflected off of a patient's cornea that occurs when the placido projector is illuminated and the handheld housing is positioned adjacent the patient's cornea wherein the ok camera provides camera signals indicative of the reflected placido image;
a display mounted on the handheld unit, that receives the camera signals and displays to the operator the reflected placido image, the display incorporating at least one alignment indicator that is positioned on the display so that the operator can move the handheld unit to orient the indicator with respect to the displayed reflected placido image into a first orientation, wherein the indicator is positioned with respect to the housing so that when the indicator is in the first orientation, the first axis of the handheld unit is in a pre-determined relationship with an optical axis of the patient's cornea; and
an image capture system that receives the camera signals wherein the image capture system captures the camera signals of the reflected placido image when the first axis of the handheld unit is in the pre-determined relationship with the optical axis of the patient's cornea wherein the captured reflected placido image is indicative of the cornea topography of the patient's cornea.

18. The system of claim 17, wherein the placido projector is comprised of a conical member having a cavity defined therein, wherein the cavity is centered about the longitudinal axis of the conical member and wherein the camera opening is also centered about the axis of the conical member.

19. The system of claim 18, wherein the placido projector is mounted within the housing so that the longitudinal axis of the conical member is substantially coaxial with the first axis of the handheld unit.

20. The system of claim 19, wherein the placido projector projects a placido image comprised of a plurality of concentric mires onto the patient's cornea when the handheld housing is positioned adjacent the cornea and the placido projector is illuminated.

21. The system of claim 20, wherein the indicator formed on the display is comprised of a pair of cross hairs that are positioned so that when the operator move the handheld housing so that the cross hairs are centered in the center of the innermost mires of the reflected placido image being displayed on the display, the axis of the placido projector is substantially coaxial with an optical axis of the patient's cornea that extends normally outward from a plane that is tangential to the patient's cornea at substantially the apex of the patient's cornea.

22. The system of claim 17, further comprising a distance measurement system that measures the distance of the handheld unit from the patient's cornea and provides a signal indicative thereof.

23. The system of claim 22, wherein the image capture system captures the camera signal of the reflected placido image upon receiving a signal that the distance measurement system has determined that the handheld housing is a first desired distance from the patient's cornea.

24. The system of claim 23, wherein the distance measurement system is comprised of:
a laser that is mounted on the housing so as to shine a beam outward from the housing in the direction of the patient's cornea when the housing is positioned so that the placido projector is positioned adjacent the patient's cornea so as to produce a reflected placido image that is being received by the camera;
a detector that is mounted in the housing so that when the handheld housing is positioned a first distance from the patient's cornea, the detector receives a pre-selected configuration of the laser beam that is being reflected from the apex of the patient's cornea.

25. The system of claim 17, further comprising a prism that receives the reflected placido image and redirects the reflected placido image so that it is projected along the second axis that is orthogonal to the first axis and wherein the camera is mounted within the housing so as to receive the reflected placido image along the second axis so that the overall dimension of the housing along the first axis can be reduced.

26. The system of claim 17, wherein the display is an LCD display.

27. The system of claim 17, further comprising a base unit that contains the image capture system and is connected to the handheld housing via a flexible cord so that the handheld unit is movable with respect to the base unit.

28. The system of claim 27, further comprising a computer that forms an image analysis system that is coupled to the base unit so as to receive the captured signals representative of the reflected placido image, wherein the computer processes these signals to obtain data reflected of the corneal topography of the patient's cornea.

29. The system of claim 17, further comprising a tilt sensor that senses the degree of tilt of the handheld housing when the reflected placido image was captured.

30. A method of obtaining corneal topography data comprising:
positioning a placido projector mounted in a handheld unit adjacent a patient's cornea;
illuminating the placido projector by inducing an electro-luminescent panel positioned adjacent the placido projector to luminesce;
sensing with a camera a reflected placido image reflected off of the patient's cornea;
displaying the reflected placido image on a display attached to the handheld unit;

moving the handheld unit until an indicator formed on the display is positioned on the displayed image in a pre-selected relationship that results in the camera being in a first orientation with respect to an axis extending through the apex of the patient's cornea;

moving the handheld unit along the axis extending through the apex of the cornea, while keeping the indicator in the pre-selected relationship with the displayed image until the handheld unit is in a pre-selected relationship along the axis with respect to the patient's cornea;

automatically capturing the reflected placido image when the indicator is in the pre-selected relationship with the displayed image and when the handheld unit is in the pre-selected relationship along the axis to the patient's cornea; and comparing the positions of a plurality of points on the reflected placido image to data representative of corresponding points on calibration models to determine the corneal topography of the cornea at the plurality of points.

31. A device for projecting a placido image for a corneal topography system, comprising:

a placido projector having an outer surface and an inner surface, the inner surface forming a cavity having mires therein; and a sheet of material disposed on said outer surface of the placido projector, wherein the sheet of material luminesces so as to illuminate the mires by passing the illumination through the placido projector.

32. The device of claim 31, wherein the placido projector is comprised of a piece of translucent material that has a cavity which defines an axis and wherein the outer surface of the placido projector extends outward from the axis at a pre-selected angle.

33. The device of claim 32, wherein the preselected angle is 37 degrees.

34. The device of claim 33, wherein the placido projector is frusto conical in shape.

35. The device of claim 34, wherein the inner cavity of the placido projector is elliptical in shape.

36. The device of claim 35, wherein the placido projector is approximately 2 inches long.

37. The device of claim 31, wherein sheet of material is comprised of a sheet of electro-luminescent (EL) panel.

38. The device of claim 31, wherein there are 9 mires formed in the inner cavity of the placido projector.

39. A method of projecting a placido image for a coneal topography system, the method comprising:

positioning a sheet of material about the outer surface of a placido projector having an inner cavity with mires formed thererin; and inducing the sheet of material to luminesce so as to illuminate the mires by passing illumination through the placido projector so as to project a placido image out of the cavity.

40. The method of claim 39, wherein the step of positioning a sheet of material about the outer surface of the placido projector comprises positioning an electro-luminescent (EL) panel about the outer surface of a placido projector formed of a piece of translucent material.

41. The method of claim 40, wherein the step of positioning a sheet of material about the outer surface of the placido projector comprises positioning the sheet of material about a frusto conical shaped placido projector.

* * * * *